US007382453B2

(12) United States Patent
Fisher et al.

(10) Patent No.: US 7,382,453 B2
(45) Date of Patent: Jun. 3, 2008

(54) APPARATUS AND METHOD FOR CHARACTERIZING AN INTERFACIAL PROPERTY OF A DISPERSION

(75) Inventors: Douglas B. Fisher, Calgary (CA); Marcel Girard, Calgary (CA)

(73) Assignee: Alberta Research Council Incorporated, Edmonton (CA)

( * ) Notice: Subject to any disclaimer, the term of this patent is extended or adjusted under 35 U.S.C. 154(b) by 276 days.

(21) Appl. No.: 11/353,574

(22) Filed: Feb. 14, 2006

(65) Prior Publication Data

US 2007/0187633 A1    Aug. 16, 2007

(51) Int. Cl.
*G01N 21/00* (2006.01)
(52) U.S. Cl. .................. 356/338; 356/337
(58) Field of Classification Search ........ 356/244–246, 356/432–448, 337–343; 250/576; 424/9.51–9.52
See application file for complete search history.

(56) References Cited

U.S. PATENT DOCUMENTS

| 4,455,860 | A | 6/1984 | Cullick et al. |
| 4,610,160 | A | 9/1986 | Christiansen |
| 4,621,522 | A | 11/1986 | Christiansen et al. |
| 4,627,273 | A | 12/1986 | Christiansen et al. |
| 4,766,558 | A | 8/1988 | Luks et al. |
| 5,505,074 | A | 4/1996 | Mihcakan et al. |
| 2005/0094127 | A1 | 5/2005 | O'mahony et al. |
| 2007/0134804 | A1* | 6/2007 | Fisher et al. ............ 436/164 |

FOREIGN PATENT DOCUMENTS

| CA | 2445426 | 4/2005 |
| JP | 05118986 A2 | 5/1993 |
| WO | 2005036181 A1 | 4/2005 |

OTHER PUBLICATIONS

Kechut, Nor Idah et. al., "New Experimental Approaches in Minimum Miscibility Pressure (MMP) Determination" SPE 57286, Society of Petroleum Engineers Inc., 1999 (6 pages).
Zain, Zahidah Md. et. al., "Evaluation of CO2 Gas Injection For Major Oil Production Fields in Malaysia . . . ," SPE 72106, Society of Petroleum Engineers Inc., 2001 (10 pages).
Takabayashi, Katsumo et. al., "Interfacial Tension Measurement between Oil and Gas Phase under High Temperature and High Pressure Condition", undated (11 pages).

* cited by examiner

*Primary Examiner*—Michael A. Lyons
*Assistant Examiner*—Tri T Ton
(74) *Attorney, Agent, or Firm*—Terrence N. Kuharchuk; Rodman & Rodman

(57) ABSTRACT

An improvement in a PVT apparatus, which improvement includes a fluid path model having a fluid path and a sampling section, wherein the depth of the fluid path within the sampling section is substantially uniform and is less than about 100 μm. The apparatus may be configured to provide a micron-scale slim tube which may be used in a manner similar to a conventional slim tube apparatus. A method for characterizing an interfacial property of a dispersion such as, for example, miscibility of a first fluid and a second fluid as a function of pressure. The method includes collecting sets of transmittance images representing transmittance of electromagnetic radiation through the dispersion, generating values of a general interfacial property factor from the transmittance images, and characterizing the interfacial property using the values of the general interfacial property factor.

57 Claims, 29 Drawing Sheets

Ethane 6.0 MPa

Ethane 13 MPa

Ethane 14 MPa

Ethane 16 MPa

Ethane 10.0 MPa

Ethane 10.5 MPa

Ethane 11.0 MPa

Ethane 11.5 MPa

Ethane 12.0 MPa

Ethane 13.0 MPa

12 MPa

14 MPa

16 MPa

APPARATUS AND METHOD FOR CHARACTERIZING AN INTERFACIAL PROPERTY OF A DISPERSION

TECHNICAL FIELD

Improvements in a PVT type apparatus and a method for characterizing an interfacial property of a dispersion using visual observation and/or image processing techniques.

BACKGROUND OF THE INVENTION

A dispersion is a system in which one or more dispersed phases are distributed throughout a dispersion medium. The dispersed phase and the dispersion medium may both be comprised of one or more solids, liquids, gases or supercritical fluids.

The study of dispersions is relevant to many fields and industries. Generally speaking, such study is often performed in order to obtain information relating to the character or nature of a particular dispersion system under selected or defined conditions.

The information obtained from such study may be used for many purposes, including for the optimization or enhancement of the composition of a particular dispersion for use under defined conditions or for the optimization or enhancement of the conditions to which a particular dispersion may be exposed in order to achieve a desired result or effect. In other words, the information may be used to tailor either or both of the composition of the dispersion or the conditions to which the dispersion may be exposed in order to achieve the desired result or effect.

The study of a dispersion often involves analysis or characterization relating to the interaction amongst the constituents of the dispersion. This interaction is influenced by the behaviour of the interfaces between the constituents, which behaviour is defined by the interfacial properties of the dispersion. The interfacial properties of a dispersion may be dependent upon time, upon the composition of the dispersion, and upon the conditions, such as pressure and temperature, to which the dispersion is subjected.

Interfacial properties may affect the stability of a dispersion as well as the relative solubility and/or miscibility of the constituents of the dispersion.

As one example, the stability of a foam or an emulsion may be governed by the interfacial properties of the constituents of the foam or emulsion. As a second example, the tendency of solid particles in a dispersion to undergo precipitation, flocculation, agglomeration or deposition may be governed by the behaviour of the solid particles relative to the dispersion medium. As a third example, the ability of a first fluid in a dispersion to mix with a second fluid in the dispersion may be governed by the interfacial properties of the first fluid and the second fluid.

Interfacial properties are important in enhanced oil recovery processes which involve fluid/gas flooding of oil reservoirs. In such processes, the goal is often to achieve miscibility between the flooding fluid (sometimes referred to as a solvent) and the hydrocarbon liquid contained in the reservoir. Miscibility is a state in which the interfaces between constituents of a dispersion essentially disappear as the interfacial tension between the constituents approaches zero.

When miscibility is achieved, the flooding fluid or solvent and the hydrocarbon liquid essentially move as a single phase so that the hydrocarbon liquid may be effectively flushed from the reservoir by the flooding fluid.

It is therefore desirable to know in advance the conditions, such as temperature and pressure, under which a dispersion comprising hydrocarbon liquid and a flooding fluid will become miscible. Of particular interest is the "minimum miscibility pressure" of the dispersion, which is the minimum pressure at which the hydrocarbon liquid and the flooding fluid will become miscible at a given temperature.

Several methods exist in the prior art for determining the minimum miscibility pressure of a dispersion in the context of enhanced oil recovery processes.

One prior art method for determining minimum miscibility pressure is the conventional Slim Tube Test. In the Slim Tube Test, a coiled slim tube apparatus about 4 millimeters to about 19 millimeters in diameter and about 15 to 20 meters long is packed with sand and then filled with a hydrocarbon liquid of interest. A volume of a flooding fluid or solvent equal to 1.2 times the pore volume of the slim tube apparatus is then injected at a constant pressure into one end of the slim tube apparatus and the volume of hydrocarbon liquid produced at the other end of the slim tube apparatus is measured. The test is repeated at different constant pressures in order to obtain at least four data points representing the produced volume of hydrocarbon liquid as a function of pressure. The minimum miscibility pressure of the hydrocarbon liquid and the flooding fluid or solvent is then determined from the data points.

Although the conventional Slim Tube Test can provide useful results, the method does have limitations. For example, the Slim Tube Test requires relatively large sample volumes, typically requires several days in order to complete each test, and has a maximum operating pressure of only about 70 MPa.

A second prior art method is the Rising Bubble Test. In the Rising Bubble Test, a discrete bubble of a flooding fluid or solvent is injected into the lower end of a windowed pressure vessel which is maintained at a constant pressure and temperature. The rising of the bubble in the vessel is observed to determine whether the bubble dissolves or dissipates before it reaches the top of the vessel. If the bubble totally dissolves, the hydrocarbon liquid/flooding fluid dispersion is considered to be miscible at the particular temperature and pressure. If the bubble does not totally dissolve, the pressure is incrementally increased and the test is repeated until the minimum miscibility pressure at the particular temperature is determined.

The Rising Bubble Test is described in U.S. Pat. No. 4,627,273 (Christiansen et al). Variations of the Rising Bubble Test are described in U.S. Pat. No. 4,610,160 (Christiansen), U.S. Pat. No. 4,621,522 (Christiansen et al), and U.S. Pat. No. 5,505,074 (Mihcakan et al).

The Rising Bubble Test requires relatively smaller sample volumes than does the Slim Tube Test and requires significantly less time than the Slim Tube Test to perform (up to ten or fifteen tests per day may be performed using a single Rising Bubble Test apparatus). However, the Rising Bubble Test has a maximum operating pressure of only about 35 MPa. In addition, since the solvent bubble must be observed "rising" in the pressure vessel, there are limitations in the types of hydrocarbon liquids which may be evaluated using the Rising Bubble Test. For example, the hydrocarbon liquid must be relatively transparent or translucent in order to permit observation of the rising bubbles and the hydrocarbon liquid must have a relatively moderate viscosity in order to facilitate rising of the bubbles therein.

Other prior art methods and approaches for determining minimum miscibility pressure in enhanced oil recovery applications are discussed in: (1) Kechut, Nor Idah; Zain, Zahidah Md.; Ahmad, Noraini; and Ibrahim, Anwar Raja, "New Experimental Approaches in Minimum Miscibility Pressure (MMP) Determination", SPE 40286, 1999; (2) Zain, Zahidah Md.; Kechut, Nor Idah; Nadeson, Ganesan; Ahmad, Noraini; Raja, Dr. D. M. Anwar, "Evaluation of $CO_2$ Gas Injection for Major Oil Production Fields in Malaysia-Experimental Approach Case Study: Dulang Field", SPE 72106, 2001; (3) U.S. Pat. No. 4,455,860 (Cullick et al); and (4) U.S. Pat. No. 4,766,558 (Luks et al).

There remains a need for an apparatus and a method for characterizing an interfacial property of a dispersion, such as minimum miscibility pressure, which addresses some or all of the limitations of the prior art apparatus and methods. There is a particular need for a method for characterizing an interfacial property of a dispersion which utilizes images and image processing techniques and for an apparatus which can be used for collecting images for processing in the method and which may also facilitate other aspects of the performance of the method.

SUMMARY OF THE INVENTION

The present invention is an apparatus and a method for use in characterizing an interfacial property of a dispersion.

The method may involve visual observation of the dispersion under different conditions in order to characterize the interfacial property of the dispersion. Preferably, however, the method utilizes images and image processing techniques in order to perform the characterization.

The apparatus provides a method of collecting images for processing in the method. The apparatus may also facilitate other aspects of the performance of the method.

The method of the invention preferably involves collecting sets of transmittance images, wherein each transmittance image represents a spatial distribution of transmittance intensity of electromagnetic radiation through a dispersion sample. The method of the invention preferably also involves processing the sets of transmittance images in order to characterize at least one interfacial property of the dispersion. As a result, the method of the invention preferably involves the application of Beer's Law.

Each set of transmittance images preferably includes transmittance images collected at a plurality of sampling times during a sampling period, during which "characterization variables" relating to the dispersion are preferably kept substantially constant. The values of one or more of the "characterization variables" may be varied in order to collect different sets of transmittance images.

The "characterization variables" may relate to the composition of the dispersion or to the conditions of the dispersion. Characterization variables relating to the composition of the dispersion may include the composition, concentration and relative proportions of the constituents of the dispersion. Characterization variables relating to the conditions of the dispersion may include the pressure of the dispersion, the temperature of the dispersion, or any other parameter relating to the conditions to which the dispersion may be exposed.

The characterization variables are related to the interfacial property or interfacial properties which are to be characterized. For example, where a characterization variable is temperature of the dispersion, the interfacial property to be characterized may be a minimum miscibility temperature of two fluids comprising the dispersion, or may be a temperature at which solid particles in a dispersion undergo precipitation, flocculation or agglomeration, or precipitation from the dispersion. Similarly, where a characterization variable is pressure of the dispersion, the interfacial property to be characterized may be a minimum miscibility pressure of two fluids comprising the dispersion, or may be a pressure at which solid particles in a dispersion undergo precipitation, flocculation or agglomeration, or precipitation from the dispersion.

In some preferred applications of the method of the invention, the characterization variables are pressure and/or temperature and the interfacial property to be characterized is either the minimum miscibility pressure or the minimum miscibility temperature of a first fluid and a second fluid comprising the dispersion.

Each set of transmittance images may be processed using image processing techniques in order to generate a value for a general interfacial property factor which is dependent upon the values of the characterization variables at which the set of transmittance images was gathered. A plurality of values of the general interfacial property factor may be generated from a plurality of sets of transmittance images and the plurality of values of the general interfacial property factor may be used to characterize one or more interfacial properties of the dispersion.

Preferably each set of transmittance images is collected relatively quickly in a manner which minimizes the required size of the dispersion sample. The apparatus of the invention facilitates relatively quick collecting of a set of transmittance images for use in certain applications of the method of the invention and requires a relatively small dispersion sample.

More particularly, the apparatus of the invention provides a fluid path for a dispersion and a sampling section through which electromagnetic radiation may be transmitted in order to produce the transmittance images. In the apparatus of the invention, the sampling section has a very shallow and substantially uniform depth in order to enable an amount of the electromagnetic radiation to be transmitted therethrough even if the dispersion is relatively non-transparent and almost opaque. The shallow and substantially uniform depth of the sampling section, such that the sampling section approaches "two-dimensions", facilitates the collection of reliable transmittance images and the analysis of a wide range of different dispersion compositions.

The apparatus of the invention is comprised of one or more improvements in a type of "PVT" apparatus, or "Pressure-Volume-Temperature" apparatus. PVT apparatus are well known in the art for use in studying pressure, volume and temperature effects on materials. PVT apparatus typically include a pressure chamber or cell with one or more viewing windows. The cell may typically be subjected to varying pressures and temperatures so that material samples placed in the cell may be studied under varying pressure and temperature conditions.

In a preferred apparatus aspect, the invention therefore relates to one or more improvements in a PVT apparatus of the type comprising a housing defining a pressure chamber, the pressure chamber having an interior and defining a viewing plane, the viewing plane having a first side and an opposed second side such that the viewing plane is contained between the first side and the second side, further comprising a first viewing window mounted in the housing substantially parallel to the viewing plane such that the first side of the viewing plane can be viewed through the first viewing window and a second viewing window mounted in the housing substantially parallel to the viewing plane such that the second side of the viewing plane can be viewed through the second viewing window.

One such improvement may be comprised of a fluid path model mounted in the interior of the pressure chamber within the viewing plane, wherein the fluid path model is comprised of a fluid path, wherein the fluid path model is further comprised of a sampling section, wherein the sampling section is comprised of at least a portion of the fluid path, wherein the fluid path within the sampling section has a substantially uniform depth in a direction substantially perpendicular to the viewing plane, and wherein the depth of the fluid path within the sampling section is less than about 100 μm. This improvement may be configured to provide a micron-scale slim tube which may be used in a manner similar to a conventional slim tube apparatus.

Other such improvements may be comprised of a source of an electromagnetic radiation associated with the first viewing window for transmitting the electromagnetic radiation through the sampling section and a transmittance sensor associated with the second viewing window for sensing a transmittance of the electromagnetic radiation through the sampling section.

The transmittance sensor is preferably comprised of an imaging device so that the transmittance sensor is capable of sensing a spatial distribution of transmittance intensity of the electromagnetic radiation through the sampling section. The imaging device is preferably adapted to collect a set of transmittance images representing the spatial distribution of transmittance intensity of the electromagnetic radiation through the sampling section at a plurality of sampling times within a sampling period. More preferably the imaging device is adapted to collect a plurality of sets of transmittance images.

Preferably the imaging device is comprised of a camera. The camera may be an analog camera or a digital camera. The camera may also be a still camera or a video camera. If the camera is an analog camera, the imaging device preferably further comprises a digitizer for converting the analog images produced by the camera to digital images.

Still other such improvements may be comprised of a memory for storing the transmittance images and a processor for processing the sets of transmittance images to characterize an interfacial property of a dispersion.

The sampling section may be comprised of all or a portion of a single longitudinal segment of the fluid path or may be comprised of all or portions of a plurality of discrete longitudinal segments of the fluid path which are spaced along all or a portion of the length of the fluid path.

The fluid path within the sampling section may be oriented in any direction which permits the depth of the fluid path to be substantially perpendicular to the viewing plane. Preferably the fluid path within the sampling section is oriented to pass a fluid therethrough in a direction which is substantially parallel to the viewing plane.

The fluid path within the sampling section may be comprised of any cross-section which permits the depth of the fluid path within the sampling section to be less than about 100 μm. For example, the fluid path may have a cross-section substantially perpendicular to the viewing plane which is substantially rectangular.

Preferably the fluid path has a width substantially parallel to the viewing plane which is significantly larger than the depth of the fluid path within the sampling section. More preferably, the ratio of the width of the fluid path to the depth of the fluid path within the sampling section is at least about 100 to 1. The sampling section may be comprised of all or a portion of a single discrete longitudinal segment of the fluid path or may be comprised of all or portions of a plurality of discrete longitudinal segments of the fluid path.

In addition, the sampling section preferably has an area substantially parallel to the viewing plane which is significantly larger than the depth of the sampling section so that the sampling section is essentially two-dimensional.

The length of the fluid path is preferably larger than the width of the fluid path. In certain "short embodiments" of the fluid path, the ratio of the length of the fluid path to the width of the fluid path is preferably at least about 2 to 1. In certain "long embodiments" of the fluid path, the ratio of the length of the fluid path to the width of the fluid path is preferably at least about 100 to 1.

The fluid path may be relatively unobstructed along its length. Preferably, however, at least a portion of the fluid path comprises obstructions therein so that the fluid path is comprised of a porous fluid path, thus simulating a porous reservoir and the tortuous flowpaths therethrough. The fluid path within the sampling section may or may not be comprised of the porous fluid path. In addition, all or only a portion of the fluid path within the sampling section may be comprised of the porous fluid path. Preferably at least a portion of the fluid path within the sampling section is comprised of the porous fluid path. It may be desirable in some applications for the sampling section to include an unobstructed portion of the fluid path in order to facilitate relatively unobstructed observation of the dispersion.

Preferably the porous fluid path is defined by an arrangement of obstructions positioned in the fluid path. The arrangement of obstructions may be placed in the fluid path or may be formed integrally with the fluid path.

Preferably, the fluid path model is comprised of a first transparent layer and a second transparent layer and the fluid path is defined by an interface formed between an interface surface of the first transparent layer and an interface surface of the second transparent layer. More preferably, the fluid path is defined by an etching on at least one of the interface surface of the first transparent layer and the interface surface of the second transparent layer.

Where the fluid path is defined by an etching, the arrangement of obstructions in the fluid path may also be defined by the etching.

In a first preferred method aspect, the invention is a method for characterizing an interfacial property of a dispersion comprising a first fluid and a second fluid, the method comprising:

(a) directing an electromagnetic radiation at the dispersion;

(b) collecting over a sampling time period a set of transmittance images representing a spatial distribution of transmittance intensity of the electromagnetic radiation through the dispersion at a plurality of sampling times within the sampling time period, while maintaining a substantially constant value of a characterization variable relating to the dispersion;

(c) repeating (a) and (b) one or more times at different values of the characterization variable in order to collect a plurality of sets of transmittance images, wherein each set of transmittance images is collected at a different value of the characterization variable;

(d) generating from each of the sets of transmittance images a value of a general interfacial property factor for the dispersion, wherein each of the values of the general interfacial property factor is associated with different values of the characterization variable; and (e) characterizing the interfacial property of the dispersion using the values of the general interfacial property factor.

In a second preferred method aspect, the invention is a method for characterizing an interfacial property of a dispersion comprising a first fluid and a second fluid, the method comprising:

(a) providing a fluid path and a sampling section, the fluid path having an inlet end and an outlet end, the sampling section comprising at least a portion of the fluid path;

(b) first introducing an initial amount of the first fluid into the fluid path so that the first fluid is contained within the fluid path;

(c) second introducing an amount of the second fluid into the inlet end of the fluid path while maintaining a substantially constant value of a characterization variable within the fluid path in order to displace the first fluid from the fluid path at the outlet end of the fluid path;

(d) directing an electromagnetic radiation at the sampling section;

(e) collecting, over a sampling time period as the first fluid is displaced from the fluid path, a set of transmittance images representing a spatial distribution of transmittance intensity of the electromagnetic radiation through the sampling section at a plurality of sampling times within the sampling time period;

(f) repeating (b) through (e) one or more times at different values of the characterization variable in order to collect a plurality of sets of transmittance images, wherein each set of transmittance images is collected at a different value of the characterization variable;

(g) generating from each of the sets of transmittance images a value of a general interfacial property factor for the dispersion, wherein each of the values of the general interfacial property factor is associated with different values of the characterization variable; and (h) characterizing the interfacial property of the dispersion using the values of the general interfacial property factor.

A distinction between the first preferred method aspect of the invention and the second preferred method aspect of the invention relates to the procedure for collecting the transmittance images. In the second preferred method aspect of the invention, the method may provide an alternative to the conventional Slim Tube Test due to the procedure for collecting the transmittance images.

The method of the invention may be performed using the apparatus of the invention or may be performed using any other apparatus or combination of apparatus which is capable of performing the method. The apparatus of the invention is, however, a preferred apparatus for use in performing the method of the invention for the reasons discussed above with respect to the apparatus of the invention, particularly when the method is performed as an alternative to the conventional Slim Tube Test.

Regardless of the apparatus or combination of apparatus which is used to perform the method, the fluid path in the second preferred method aspect is preferably is sized in cross-section and length to minimize the sample size which is required to perform the method, to minimize the time which is required to perform the method, and to maximize the transmittance of the electromagnetic radiation through the dispersion in the sampling section.

Although the fluid path in the second preferred method aspect may be relatively unobstructed, preferably at least a portion of the fluid path in the second preferred method aspect is comprised of a porous fluid path, particularly where the method is being used to characterize the minimum miscibility pressure and/or minimum miscibility temperature of a dispersion comprising a hydrocarbon liquid and a flooding fluid or solvent. The porous fluid path provides a simulation of a hydrocarbon reservoir in a porous medium such as sand, and the associated tortuous flowpaths therethrough, in a similar manner as the conventional slim tube apparatus.

More preferably, at least a portion of the sampling section in the second preferred method aspect is comprised of the porous fluid path.

The porous fluid path may be provided by forming or placing an arrangement of obstructions within the fluid path or by forming an arrangement of obstructions integrally with the fluid path. In circumstances where the fluid path is very small in cross-section, the arrangement of obstructions is preferably formed integrally with the fluid path.

In all aspects, the dispersion which is subjected to the method of the invention may be comprised of any dispersion system which includes a first fluid and a second fluid. The dispersion may include more than two fluids and may or may not include solid particles. The fluids may be liquids, gases or supercritical fluids.

In preferred embodiments of the application of the method of the invention, the first fluid is comprised of a hydrocarbon liquid such as a crude oil (which may or may not include solid particles such as asphaltenes and other impurities), and the second fluid is comprised of a flooding fluid or solvent of the type which may be used in enhanced oil recovery processes. For example, the second fluid may be comprised of one or more gaseous or supercritical aliphatic hydrocarbons such as ethane, propane, pentane etc. and/or may be comprised of one or more other gases or supercritical fluids such as carbon dioxide.

The aspects and embodiments of the method of the invention described herein may be applied to characterize various interfacial properties of the dispersion, since the method of the invention is directed generally at the use of transmittance images to obtain information regarding the interaction between the first fluid and the second fluid.

For example, the method of the invention may be applied to characterize the stability of foams and emulsions or to characterize the conditions under which asphaltenes may precipitate, flocculate, agglomerate or deposit from a dispersion comprising a hydrocarbon liquid. Alternatively and in the preferred embodiments described herein, the method of the invention may be used to determine minimum miscibility pressure and/or minimum miscibility pressure of the first fluid and the second fluid.

The electromagnetic radiation may be comprised of radiation of any wavelength which is capable of exhibiting transmittance through the dispersion. Transmittance of the electromagnetic radiation through the dispersion is required for the practice of the invention because the method of the invention relies upon the relationships described by Beer's Law, which allows for the conversion of transmittance data into a measure of the concentrations in the dispersion of the constituents of the dispersion.

Preferably the wavelength of the electromagnetic radiation is selected having regard to the characteristics of the dispersion. For example, where the dispersion is comprised of hydrocarbon liquid, particularly crude oil, wavelengths within the visible or infrared portion of the electromagnetic spectrum may be preferred.

The wavelength or wavelengths of the electromagnetic radiation which is observed in the transmittance images may be controlled by using one or more filters either to control the transmittance of the electromagnetic radiation through the dispersion or to control the collection of the transmittance images after the electromagnetic radiation has been transmitted through the dispersion.

For example, in the preferred embodiments, an optical filter may be provided between the source of the electromagnetic radiation and the imaging device, either by attachment to the lens of the imaging device, or in some other manner. The optical filter may be selected having regard to the composition of the dispersion and the ease with which the transmittance of electromagnetic radiation of various wavelengths can be observed.

The number of values of the general interfacial property factor which are generated in order to characterize the interfacial property of the dispersion may depend upon the composition of the dispersion, the selection of the characterization variable or variables, and the interfacial property which is being characterized. Preferably at least four values of the general interfacial property factor are generated in order to provide a suitable number of data points from which to characterize the interfacial property of the dispersion.

The sampling time period over which each set of transmittance images is collected may be any time period which will provide sufficient data to effectively generate the value of the general interfacial property factor from the set of transmittance images. The number of sampling times and thus the number of transmittance images which are collected during the sampling time period is dependent upon such considerations as the time sensitivity of the general interfacial property factor, the desired resolution of the general interfacial property factor, and the data processing capabilities of the apparatus which is used to perform the method. In general, the sampling time period and the number of transmittance images which is collected within a set of transmittance images are preferably the minimum which is required to provide reliable data from which to generate the value of the general interfacial property factor.

In preferred embodiments, the method of the invention may be refined to provide variations of the method. In a first preferred embodiment, the method may be referred to as the "Image Histogram Method". In a second preferred embodiment, the method may be referred to as the "Direct Frequency Domain Method". In a third preferred embodiment, the method may be referred to as the "Derivative Image Frequency Domain Method". Each of these three preferred embodiments provides a different procedure for generating the values of the general interfacial property factor as provided for in the method of the invention, and other procedures for generating the values of the general interfacial property factor may also be used within the scope of the method of the invention.

In all embodiments of the method of the invention, the sets of transmittance images may be subjected to one or more preliminary image conditioning procedures before generating the values of the general interfacial property factor in order to enhance the performance of the method and the results obtained from the method.

In a first preliminary image conditioning procedure, each set of transmittance images may be processed to provide an intensity spatial correction of the sets of transmittance images to account for variations in a spatial distribution of intensity of the electromagnetic radiation being directed at the sampling section.

The first preliminary image conditioning procedure may be comprised of collecting a background transmittance image and using the background transmittance image to correct each of the transmittance images, wherein the background transmittance image represents a spatial distribution of transmittance intensity of the electromagnetic radiation through the sampling section without influence from the first fluid and the second fluid.

Using the background transmittance image to correct each of the transmittance images may be comprised of subtracting the background transmittance image from each of the transmittance images or may be comprised of dividing the background transmittance image into each of the transmittance images. Preferably the background transmittance image is divided into each of the transmittance images in order to normalize the transmittance images in accordance with Beer's Law.

In a second preliminary image conditioning procedure, each set of transmittance images may be processed to provide an intensity time correction of the sets of transmittance images to account for variations over time in the intensity of the electromagnetic radiation being directed at the sampling section.

The second preliminary image conditioning procedure may be comprised of producing a histogram representing each of the transmittance images, wherein each of the histograms provides a relationship between transmittance intensity and frequency of transmittance intensity throughout the transmittance image at one of the sampling times.

The second preliminary image conditioning procedure may be further comprised of processing each of the histograms to produce cumulative frequency distributions for each of the histograms, wherein each of the cumulative frequency distributions provides a relationship between transmittance intensity and frequency of transmittance intensity throughout the transmittance image at one of the sampling times.

The second preliminary image conditioning procedure may be further comprised of processing the cumulative frequency distributions below a lower cumulative frequency threshold and above an upper cumulative frequency threshold in order to provide the intensity time correction.

The second preliminary image conditioning procedure may be further comprised of determining a lower limit transmittance intensity for each of the cumulative frequency distributions at the lower cumulative frequency threshold, adjusting transmittance intensities below the lower cumulative frequency threshold in each of the cumulative frequency distributions to the lower limit transmittance intensity, determining an upper limit transmittance intensity for each of the cumulative frequency distributions at the upper cumulative frequency threshold, adjusting transmittance intensities above the upper cumulative frequency threshold in each of the cumulative frequency distributions to the upper limit transmittance intensity, and then regenerating the sets of transmittance images using the adjusted transmittance intensities so that the regenerated sets of transmittance images include the intensity time correction.

The lower cumulative frequency threshold may be selected at some arbitrary value such as one (1%) percent or five (5%) percent. Similarly, the upper cumulative frequency threshold may be selected at some arbitrary value such as ninety-five (95%) percent or ninety nine (99%) percent. In any event, the goal in selecting the cumulative frequency thresholds is to adjust those transmittance intensities which do not provide any useful information relating to the changes in the external experimental controls and conditions, since these adjusted transmittance intensities may be considered as "noise".

Preferably the sets of transmittance images are subjected to both the first preliminary image conditioning procedure and the second preliminary image conditioning procedure before the values of the general interfacial property factor are generated from the transmittance images. Other preliminary image conditioning procedures may also be used in addition to or in the place of the first preliminary image conditioning procedure and the second preliminary image conditioning procedure.

In the Image Histogram Method of the invention, generating the value of the general interfacial property factor from a set of transmittance images is comprised of producing a histogram representing each transmittance image in a set of transmittance images and then determining the value of the general interfacial property factor for the set of transmittance images from the histograms. In the Image Histogram Method, each of the histograms provides a frequency relationship between transmittance intensity and frequency of transmittance intensity throughout one of the transmittance images at the particular sampling time at which the transmittance image was collected.

In the Image Histogram Method, determining the value of the general interfacial property factor from the histograms may be comprised of identifying in each of the histograms a peak which represents transmittance intensity of the electromagnetic radiation through one of the first fluid and the second fluid and then using the peaks to determine the value of the general interfacial property factor.

Determining the value of the general interfacial property factor from the histograms in the Image Histogram Method may more particularly be comprised of calculating a peak area for each of the peaks, determining a first relationship between the peak areas and the sampling times, and using the first relationship to determine the value of the general interfacial property factor.

For example, the general interfacial property factor may be an endpoint first peak area which is identified from the first relationship. Alternatively, the general interfacial property factor may be some other quantity which is derived from the first relationship and which is representative of the interfacial property to be characterized.

In an alternative application of the Image Histogram Method, determining the value of the general interfacial property factor from the histograms may be comprised of identifying in each of the histograms a first peak which represents transmittance intensity of the electromagnetic radiation through the first fluid, identifying in each of the histograms a second peak which represents transmittance intensity of the electromagnetic radiation through the second fluid, and then using both the first peaks and the second peaks to determine the value of the general interfacial property factor.

In this alternative application of the Image Histogram Method, determining the value of the general interfacial property factor from the histograms may more particularly be comprised of calculating a first peak area for each of the first peaks, calculating a second peak area for each of the second peaks, determining a first relationship between the first peak areas, the second peak areas and the sampling times, and using the first relationship to determine the value of the general interfacial property factor. Determining the first relationship may be comprised of calculating peak area ratios between the first peak areas and the second peak areas for each of the first peak areas and each of the second peak areas.

For example, the general interfacial property factor may be an endpoint peak area ratio which is identified from the first relationship. Alternatively, the value of the general interfacial property factor may be some other quantity which is derived from the first relationship and which is representative of the interfacial property to be characterized.

In the Direct Frequency Domain Method of the invention, generating the value of the general interfacial property factor from a set of transmittance images is comprised of transforming each transmittance image into a frequency domain to produce a transformed transmittance image and then determining the value of the general interfacial property factor for the set of transmittance images from the transformed transmittance images. In the Direct Frequency Domain Method, each of the transformed transmittance images provides a frequency relationship between transmittance intensity and frequency of transmittance intensity throughout one of the transmittance images at the particular sampling time at which the transmittance image was collected. In other words, each of the transformed transmittance images represents a two-dimensional frequency domain power spectrum.

In the Direct Frequency Domain Method, determining the value of the general interfacial property factor from the transformed transmittance images may be comprised of identifying in each of the transformed transmittance images a frequency region of interest and then using the frequency region of interest to determine the value of the general interfacial property factor. The same frequency region of interest is used for all of the transformed transmittance images.

Determining the value of the general interfacial property factor from the transformed transmittance images in the Direct Frequency Domain Method may more particularly be comprised of calculating a frequency region integral for the frequency region of interest of each of the transformed transmittance images, determining a first relationship between the frequency region integrals and the sampling times, and using the first relationship to determine the value of the general interfacial property factor.

For example, the general interfacial property factor may be an endpoint frequency region integral which is identified from the first relationship. Alternatively, the value of the general interfacial property factor may be an average frequency region integral which is identified from the first relationship, an integral of the first relationship, or some other quantity which is derived from the first relationship and which is representative of the interfacial property to be characterized.

The entire transformed transmittance image may be selected as the frequency region of interest. Typically, however, only portions of the transformed transmittance image will contain information which is useful for characterizing the interfacial property of the dispersion. As a result, preferably only the portion of the transformed transmittance image which contains useful information is selected as the frequency region of interest.

The selection of the frequency region of interest in the Direct Frequency Domain Method may also be dependent upon the composition of the dispersion, the characterization variables, and the interfacial property to be characterized. Generally, however, the relatively low frequency regions of the transformed transmittance image will contain the most important and useful information for characterizing the interfacial property of the dispersion.

Specifically, in applications of the Direct Frequency Domain Method where the dispersion is comprised of a first fluid and a second fluid, where the characterization variable is pressure or temperature, and where the interfacial property is minimum miscibility pressure or minimum miscibility temperature, it has been found that the frequency region of interest preferably consists essentially of relatively low frequencies.

Stated otherwise, preferably the frequency region of interest is between zero and an upper frequency limit, so that frequencies above the upper frequency limit are excluded from the frequency region of interest.

In quantitative terms, the ratio of the area of the frequency region of interest to the area of the transformed transmittance image is preferably no greater than a selected threshold ratio value. In preferred embodiments of the method of the invention, the selected threshold ratio value is preferably 0.5:1, is more preferably 0.25:1, and may be as small as 0.1:1. These ratios are exemplary only, and a more important consideration in selecting the frequency region of interest is identifying the portion of the transformed transmittance image which contains useful information about the interfacial property of the dispersion.

In the Derivative Image Frequency Domain Method of the invention, generating the value of the general interfacial property factor from a set of transmittance images is comprised of producing a set of derivative transmittance images, transforming each derivative transmittance image into a frequency domain to produce a transformed derivative transmittance image and then determining the value of the general interfacial property factor for the set of transmittance images from the transformed derivative transmittance images.

In the Derivative Image Frequency Domain Method, each of the derivative transmittance images represents a spatial distribution of a difference in transmittance intensity of the electromagnetic radiation between a pair of the transmittance images collected at a pair of the sampling times separated by a time interval, and each of the transformed derivative transmittance images provides a frequency relationship between the difference in transmittance intensity and frequency of the difference in transmittance intensity throughout the derivative transmittance image during the time interval defined by the pair of the sampling times. Preferably the time interval defined by the pair of sampling times for each derivative transmittance image is the same. Each of the transformed derivative transmittance images represents a two-dimensional frequency domain power spectrum of its associated derivative transmittance image.

In the Derivative Image Frequency Domain Method, determining the value of the general interfacial property factor from the transformed derivative transmittance images may be comprised of identifying in each of the transformed derivative transmittance images a frequency region of interest and then using the frequency region of interest to determine the value of the general interfacial property factor. The same frequency region of interest is used for all of the transformed derivative transmittance images.

Determining the value of the general interfacial property factor from the transformed derivative transmittance images in the Derivative Image Frequency Domain Method may more particularly be comprised of calculating a frequency region integral for the frequency region of interest of each of the transformed transmittance images, determining a first relationship between the frequency region integrals and the sampling times, and using the first relationship to determine the value of the general interfacial property factor.

For example, the general interfacial property factor may be an endpoint frequency region integral which is identified from the first relationship. Alternatively, the value of the general interfacial property factor may be an average frequency region integral which is identified from the first relationship, an integral of the first relationship, or some other quantity which is derived from the first relationship and which is representative of the interfacial property to be characterized.

The selection of the frequency region of interest in the Derivative Image Frequency Domain Method is dependent upon the same considerations as in the Direct Frequency Domain Method.

Regardless of how the values of the general interfacial property factor are generated, characterizing the interfacial property of the dispersion in the method of the invention may be comprised of determining a second relationship between the values of the general interfacial property factor and the values of the characterization variable and then characterizing the interfacial property of the dispersion using the second relationship.

Characterizing the interfacial property of the dispersion using the second relationship may more particularly be comprised of identifying from the second relationship a transition value of the characterization variable, wherein the interfacial property is the transition value of the characterization variable.

In preferred embodiments of the method of the invention where the characterization variable is pressure and the interfacial property to be characterized is minimum miscibility pressure, characterizing the interfacial property of the dispersion from the second relationship may be comprised of identifying from the second relationship a transition pressure, wherein the minimum miscibility pressure is the transition pressure.

BRIEF DESCRIPTION OF DRAWINGS

Embodiments of the invention will now be described with reference to the accompanying drawings, in which:

FIG. 12(a), FIG. 12(b) and FIG. 12(c) are exemplary histograms as would be produced in the Image Histogram Method of the invention, in which FIG. 12(a) is a histogram representing a transmittance image taken at the beginning of a sampling time period, FIG. 12(b) is a histogram representing a transmittance image taken at an intermediate sampling time within a sampling time period, and FIG. 12(c) is a histogram representing a transmittance image taken at the end of a sampling time period.

DETAILED DESCRIPTION

The invention includes improvements in a PVT type apparatus and a method for characterizing an interfacial property of a dispersion.

In the preferred embodiments of the invention described herein, the method is performed according to the second preferred method aspect of the invention using the apparatus of the invention. In the preferred embodiments, the dispersion is comprised of a first fluid and a second fluid, wherein the first fluid is comprised of a hydrocarbon liquid and the second fluid is comprised of a suitable flooding fluid or solvent comprising one or more gases and/or supercritical fluids, such as, for example, ethane, propane, carbon dioxide or mixtures thereof. In the preferred embodiments, the interfacial property to be characterized is a minimum miscibility pressure of the first fluid and the second fluid.

Figure 1:
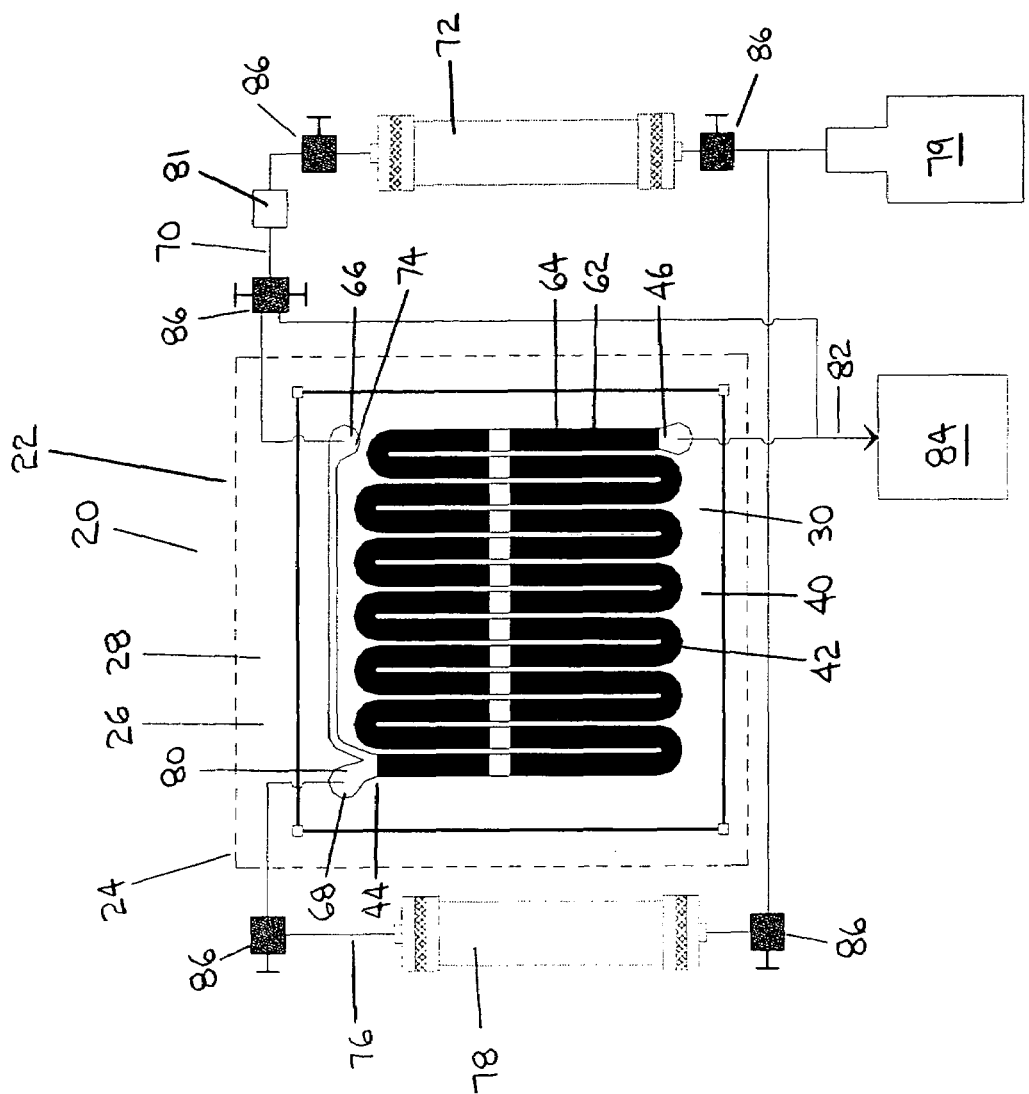
FIG. 1 is a schematic drawing of a fluid testing system according to a preferred embodiment of the apparatus of the invention, including a long embodiment of a fluid path.

Referring to FIG. 1, a schematic drawing of a fluid testing system (20) is provided. The fluid testing system (20) includes a preferred embodiment of a PVT apparatus (22) which includes improvements according to an apparatus aspect of the invention.

Figure 2:
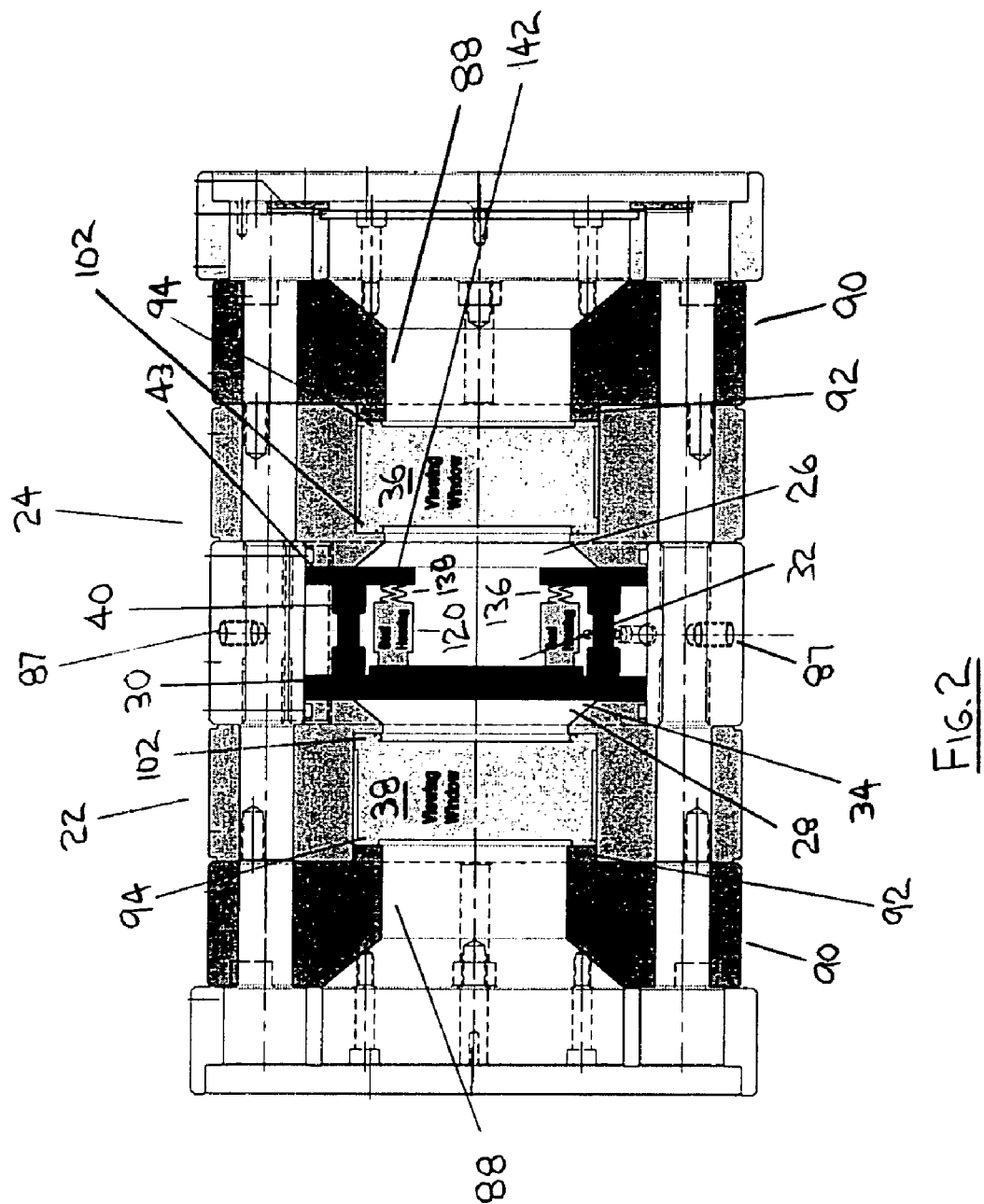
FIG. 2 is a section drawing of components of a PVT apparatus according to a preferred embodiment of the apparatus of the invention.
Figure 3:
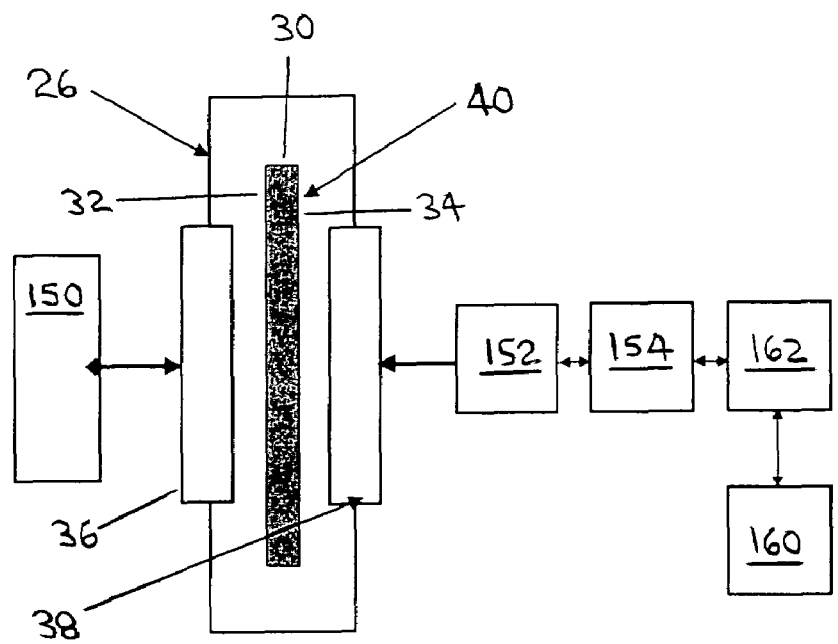
FIG. 3 is a schematic drawing of a PVT apparatus according to a preferred embodiment of the apparatus of the invention.

Referring to FIG. 2, a section drawing of components of the PVT apparatus (22) is provided. Referring to FIG. 3, a schematic drawing of the PVT apparatus (22) is provided.

The PVT apparatus (22) is comprised of a housing (24) which defines a pressure chamber (26). The pressure chamber (26) has an interior (28) and defines a viewing plane (30). The viewing plane (30) has a first side (32) and an opposed second side (34) so that the viewing plane (30) is contained between the first side (32) and the second side (34). In the preferred embodiments the housing (24) is constructed of a metal.

The PVT apparatus (22) is further comprised of a first viewing window (36) mounted in the housing (24) substantially parallel to the viewing plane (30) such that the first side (32) of the viewing plane (30) can be viewed through the first viewing window (36). Similarly, the PVT apparatus (22) is further comprised of a second viewing window (38) mounted in the housing (24) substantially parallel to the viewing plane (30) such that the second side (34) of the viewing plane (30) can be viewed through the second viewing window (38).

The viewing windows (36,38) are selected to be transparent to the particular electromagnetic radiation which is to be used in the method of the invention. In the preferred embodiments the viewing windows (36,38) are preferably constructed of sapphire or glass, but may be constructed of a suitable transparent plastic.

Referring to FIGS. 2 and 3, a preferred embodiment of a fluid path model (40) according to the invention is mounted in the interior (28) of the pressure chamber (26) and within the viewing plane (30). The fluid path model (40) is comprised of a fluid path (42) which is held by a fluid path model frame (43). The fluid path (42) has an inlet end (44) and an outlet end (46).

The fluid path model (40) is further comprised of a sampling section (48) located between the inlet end (44) and the outlet end (46) of the fluid path (42). The sampling section (48) is comprised of at least a portion of the fluid path (42). In the preferred embodiments, the sampling section (48) is oriented in the housing (24) to pass a fluid therethrough in a direction which is substantially parallel to the viewing plane (30).

The width, length and configuration of the fluid path (42) may vary depending upon the intended use of the PVT apparatus (22) and the method to be performed by the PVT apparatus (22).

Figure 7:
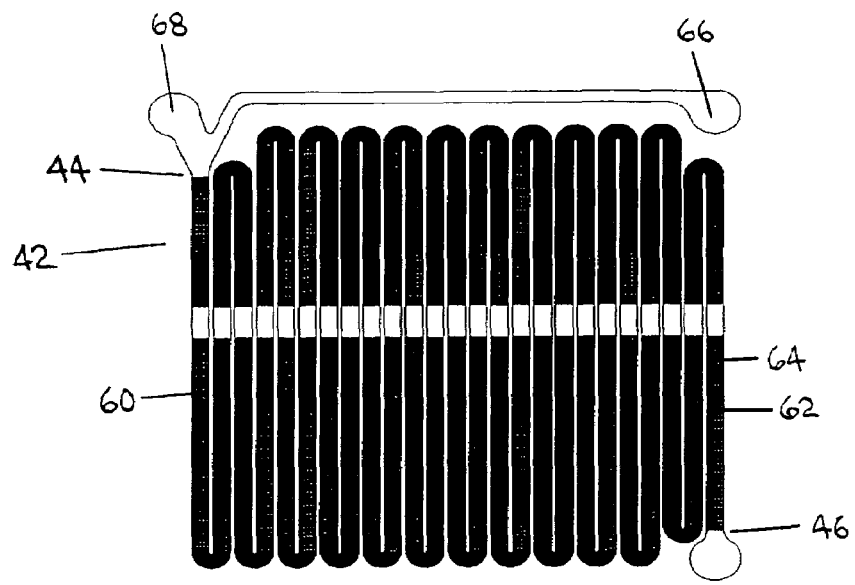
FIG. 7 is a schematic drawing of a long embodiment of a fluid path according to a preferred embodiment of the apparatus of the invention.
Figure 9:
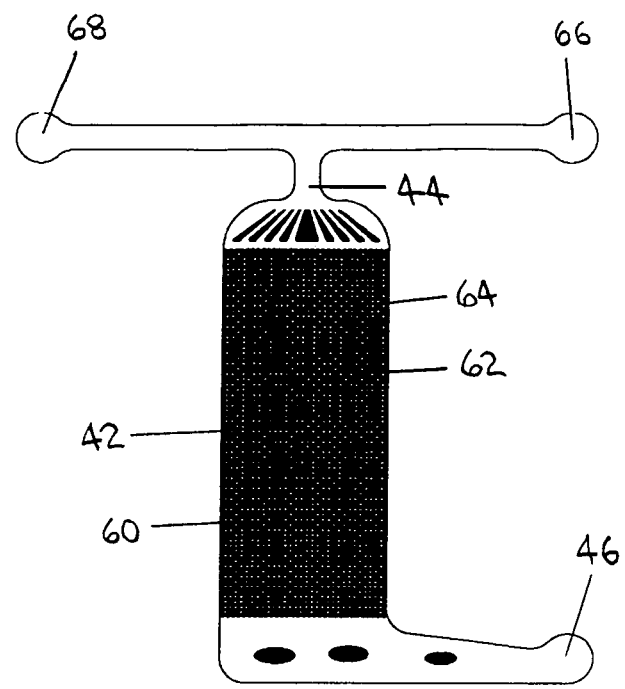
FIG. 9 is a schematic drawing of a short embodiment of a fluid path according to a preferred embodiment of the apparatus of the invention.

FIG. 7 depicts one preferred embodiment of the fluid path (42) and FIG. 9 depicts a second preferred embodiment of the fluid path (42) as examples only of possible widths, lengths and configurations of the fluid path (42).

In FIG. 7, the fluid path (42) is a "long embodiment" in which the length of the fluid path (42) is significantly greater than the width of the fluid path (42). For example, the length of the fluid path (42) in the long embodiment depicted in FIG. 7 may be between about 0.75 meters and about 1.3 meters and the width of the fluid path (42) in the long embodiment may be about 4 millimeters. The long embodiment of the fluid path (42) may proportionately approximate or simulate a conventional slim tube apparatus used in the Slim Tube Test in which the length of the fluid path may be between about 15 and 20 meters and the diameter of the fluid path may be between about 4 millimeters and about 19 millimeters.

Figure 8:
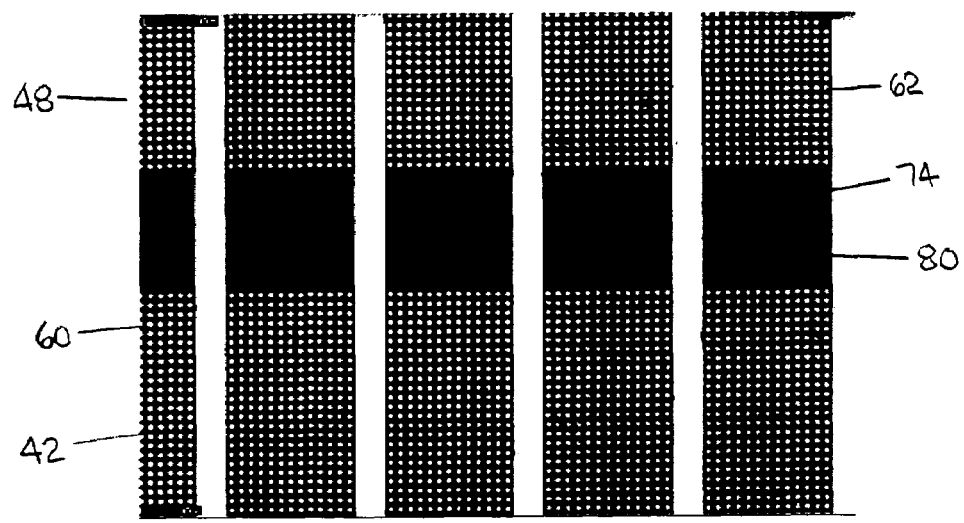
FIG. 8 is an exemplary transmittance image as would be collected using a fluid path of the type depicted in FIG. 7.

FIG. 8 provides an exemplary transmittance image as would be collected using a fluid path (42) of the type depicted in FIG. 7.

In FIG. 9, the fluid path (42) is a "short embodiment" in which the width of the fluid path (42) is significantly greater than the width of the fluid path (42) in the long embodiment and in which the length of the fluid path (42) is significantly shorter than the length of the fluid path (42) in the long embodiment. For example, the width of the fluid path (42) in the short embodiment depicted in FIG. 9 may be about 20 millimeters and the length of the fluid path (42) in the short embodiment may be about 45 millimeters.

Figure 10:
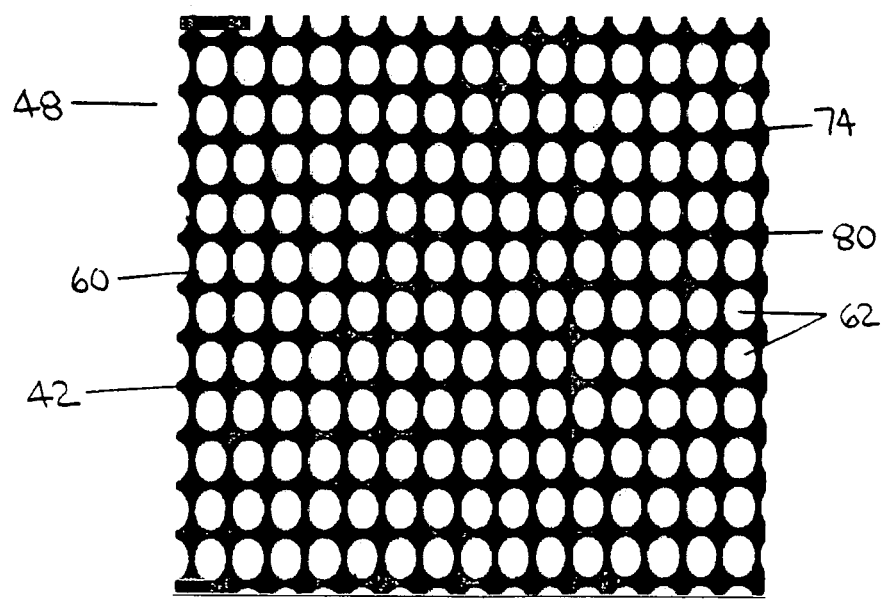
FIG. 10 is an exemplary transmittance image as would be collected using a fluid path of the type depicted in FIG. 9.

FIG. 10 provides an exemplary transmittance image as would be collected using a fluid path (42) of the type depicted in FIG. 9.

The sampling section (48) is comprised of at least a portion of the fluid path (42). The sampling section (48) may be comprised of any portion of the fluid path (42) between the inlet end (44) and the outlet end (46). The sampling section (48) may be fixed or the sampling section (48) may move during use of the fluid path model (40). For example, the sampling section (48) may be comprised of a single discrete longitudinal segment of the fluid path (42) which is either fixed or movable over time. The sampling section (48) may also be comprised of a plurality of discrete longitudinal segments along the width or length of the fluid path (42). Configuring the sampling section (48) so that it is comprised of a plurality of discrete longitudinal segments or so that it moves over time may facilitate enhanced capabilities of the PVT apparatus (22) or of the method of the invention.

Referring to FIG. 8, the sampling section (48) is comprised of a plurality of discrete longitudinal segments of the fluid path (42). Referring to FIG. 10, the sampling section (48) is comprised of a single discrete longitudinal segment of the fluid path (42) which may or may not extend for the full width of the fluid path (42).

In all embodiments of the fluid path (42), the fluid path (42) within the sampling section (48) has a substantially uniform depth which is measured in a direction substantially perpendicular to the viewing plane (30). The depth of the fluid path (42) within the sampling section (48), is minimized so that the sampling section (48) approaches "two-dimensions" in a plane parallel to the viewing plane (30). In practical terms, the depth of the sampling section (48) is preferably less than about 100 µm. An essentially two-dimensional sampling section (48) enables use of the PVT apparatus (22) with fluids that are relatively opaque or non-transparent, and a substantially uniform depth of the sampling section (48) provides for the collection of consistent and uniform data over the entire area of the sampling section (48).

Figure 5:
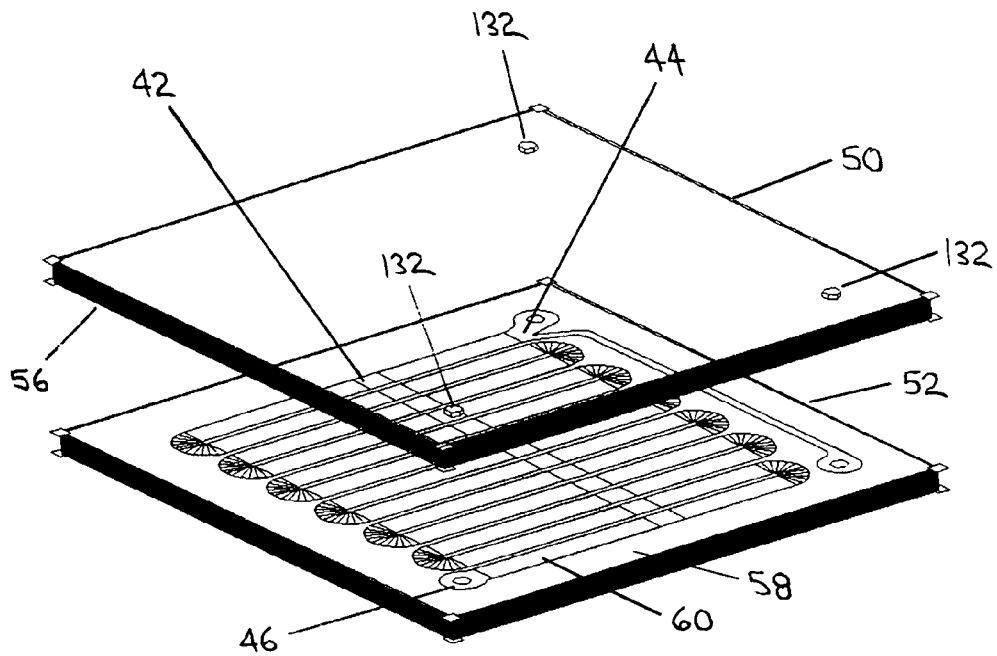
FIG. 5 is an exploded pictorial drawing of a fluid path model according to a preferred embodiment of the apparatus of the invention, including a long embodiment of a fluid path.

Referring to FIG. 5, in the preferred embodiments the fluid path model (40) is further comprised of a first transparent layer (50) and a second transparent layer (52) and the fluid path is defined by an interface (54) formed between an interface surface (56) of the first transparent layer (50) and an interface surface (58) of the second transparent layer (52). In the preferred embodiments, the first transparent layer (50) and the second transparent layer (52) are comprised of glass and the fluid path (42) is defined by an etching (60) on at least one of the interface surfaces (56,58).

Referring to FIGS. 7-10, in the preferred embodiments at least a portion of the fluid path (42) includes an arrangement of obstructions (62) therein so that at least a portion of the fluid path (42) is comprised of a porous fluid path (64). The obstructions (62) disrupt the flow of fluids through the fluid path (42) and cause the fluid path (42) to simulate tortuous flowpaths in a porous formation such as a hydrocarbon reservoir.

In the preferred embodiments, the obstructions (62) are formed integrally with the fluid path (42) and are defined by the etching (60) as an arrangement of protrusions such as pillars in the fluid path (42). The protrusions may be any shape which provide desired fluid flow characteristics through the fluid path (42), but in the preferred embodiments the protrusions are round or polygonal in cross-section. The protrusions may be arranged in any configuration, but in the preferred embodiments the protrusions are arranged generally in rows and/or columns.

Referring to FIGS. 7 and 9, the inlet end (44) of the fluid path (42) is comprised of a first fluid inlet (66) and a second fluid inlet (68).

Referring to FIG. 1, the first fluid inlet (66) is connected by a first fluid line (70) with a source (72) of a first fluid (74) and the second fluid inlet (68) is connected by a second fluid line (76) with a source (78) of a second fluid (80). A pump (79) is associated with the sources (72,78) for introducing the fluids (74,80) into the fluid path (42). An in-line filter (81) is provided in the first fluid line (70) in order to filter the first fluid (74) before it is introduced into the fluid path (42).

Referring to FIG. 1, the outlet end (46) of the fluid path (42) is connected with an outlet fluid line (82) for expelling the first fluid (74) and the second fluid (80) from the fluid path (42). A back pressure regulator (84) is associated with the outlet fluid line (82) so that a desired pressure may be maintained within the fluid path (42).

A plurality of valves (86) is provided throughout the fluid testing system (20) to control the introduction of the first fluid (74) and the second fluid (80) into the fluid path (42) and the expulsion of the first fluid (74) and the second fluid (80) from the fluid path (42).

Referring to FIG. 2, the first fluid line (70), the second fluid line (76) and the outlet fluid line (82) pass through sealed ports (87) in the PVT apparatus (22) in order to connect with the first fluid inlet (66), the second fluid inlet (68) and the outlet end (46) of the fluid path (42) respectively.

The PVT apparatus (22) is capable of containing pressures of 140 MPa or more, which pressures are provided by an overburden fluid (not shown) such as water which fills the pressure chamber (26). Such pressures place high demands upon the interfaces between the glass viewing windows (36,38) and the metal housing (24), due in part to the dissimilarity of materials.

As a result, in the preferred embodiments the PVT apparatus (22) includes a window mounting assembly (88) for each of the viewing windows (36,38) which compensates for this dissimilarity of materials.

Figure 4:
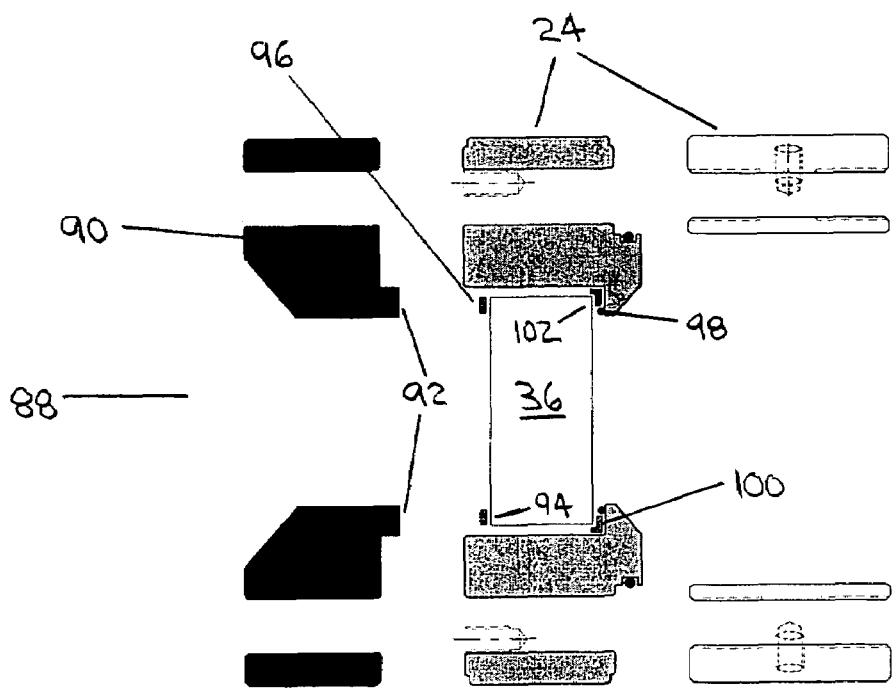
FIG. 4 is an isolated exploded section drawing of a window mounting assembly according to a preferred embodiment of the apparatus of the invention.

Referring to FIGS. 2 and 4, each window mounting assembly (88) is comprised of a viewing window flange (90) which may be bolted, screwed or threaded to the housing (24). The viewing window flange (90) includes a window engagement surface (92) which is adapted to engage an outer peripheral edge (94) of the viewing window (36,38) in order to press the viewing window (36,38) against the outer surface of the housing (24). Each window mounting assembly (88) is further comprised of a resilient backup ring (96) which is positioned between the window engagement surface (92) and the outer peripheral edge (94) of the viewing window (36,38) in order to cushion the viewing window (36,38) during pressurization of the PVT apparatus (22), thus reducing stresses on the viewing window (36,38) which could cause failure of the viewing window (36,38). In preferred embodiments the resilient backup ring (96) may be constructed of a polyether ether ketone (PEEK), which is well known for its elastic deformation properties. Where the resilient backup ring (96) may be exposed to very high temperatures, the resilient backup ring (96) may more preferably be constructed of annealed copper or of some other material which can sustain very high temperatures.

The window mounting assembly (88) is further comprised of a viewing window seal (98) such as an O-ring seal which is located between the housing (24) and the viewing window (36,38) and which is maintained in position by a locating gasket (100) which extends around an inner peripheral edge (102) of the viewing window (36,38). In the preferred embodiments the locating gasket (100) is constructed of a polyether ether ketone (PEEK).

Similarly, challenges exist in connecting the first fluid line (70), the second fluid line (76) and the outlet fluid line (82) with the fluid path model (40), due to the pressures exerted on the fluid path model (42) during use of the PVT apparatus (22). In the preferred embodiments, each of these fluid lines (70,76,82) is connected with the fluid path model (40) using a fluid line fitting (120).

Figure 6:
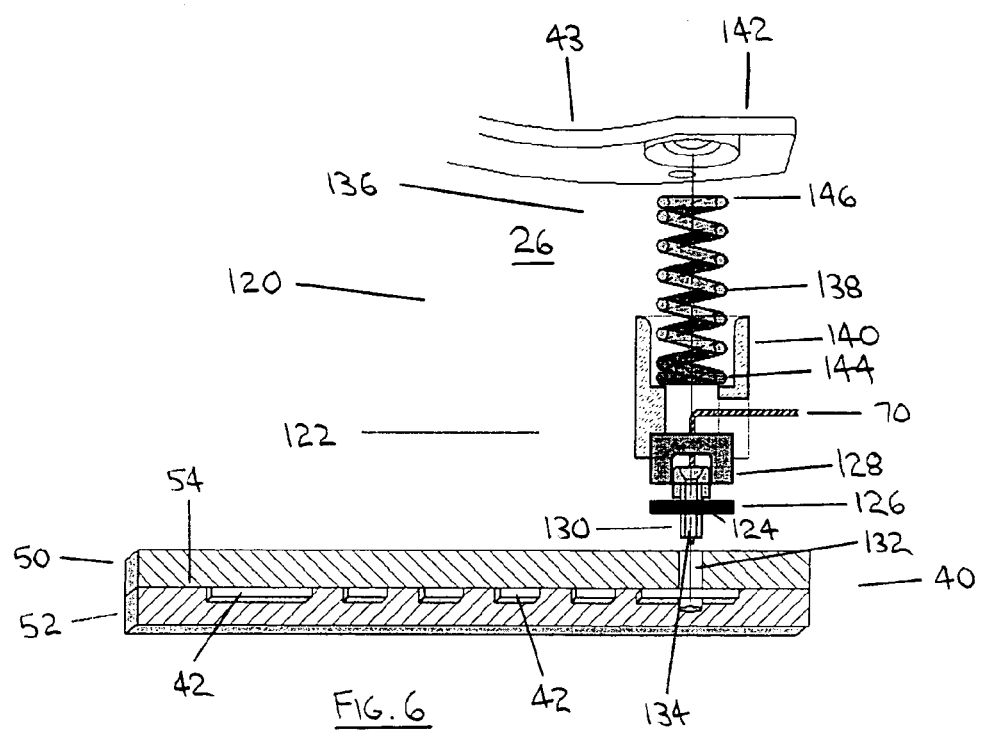
FIG. 6 is a schematic drawing of a fluid line fitting according to a preferred embodiment of the apparatus of the invention.

Referring to FIGS. 2 and 6, each of the fluid line fittings (120) is comprised of a fluid line coupler (122) which is connected with one of the fluid lines (70,76, or 82). The fluid line coupler (122) is comprised of a transparent layer engagement surface (124). The transparent layer engagement surface (124) is comprised of a fluid path seal (126) which abuts the first transparent layer (50) in order to provide a seal between the fluid line coupler (122) and the first transparent layer (50).

The fluid line coupler (122) is further comprised of a pressure member (128) for exerting an engagement force on the first transparent layer (50) to urge the fluid line coupler (122) against the first transparent layer (50). When the pressure chamber (26) is pressurized, the engagement force is comprised of a force exerted on the pressure member (128) by the overburden fluid.

A resilient spacer insert (130) is provided between the fluid path seal (126) and the pressure member (128) in order to cushion the first transparent layer (50) against forces or reaction forces exerted upon the first transparent layer (50) by the fluid line coupler (122) and in order to assist in maintaining the integrity of the seal between the fluid path seal (126) and the first transparent layer (50).

The resilient spacer insert (130) fits within an aperture (132) in the first transparent layer (50) so that the resilient spacer insert (130) effectively seals the aperture (132) and plugs the aperture (132) so that the fluid path seal (126) does not tend to be pressed into the aperture (132) when the pressure chamber (26) is pressurized. The fluid line (70,76 or 82) extends through a bore (134) of the resilient spacer insert (127) and thus through the aperture (132) in the first transparent layer (50) so that the fluid line (70,76, or 82) is in communication with the fluid path (42).

In the preferred embodiments, the resilient spacer insert (130) is constructed of a polyether ether ketone (PEEK). In the preferred embodiments, the pressure member (128) and the resilient spacer insert (130) are capable of an amount of relative longitudinal movement to provide further protection of the first transparent layer (50) in the event of expansion, contraction or other movement of the pressure member (128) and/or the resilient spacer insert (130).

In the preferred embodiments the fluid line coupler (122) is also provided with a preloading mechanism (136) so that the fluid line coupler (122) is urged against the first transparent layer (50) even when the pressure chamber (26) is not pressurized. In the preferred embodiments the preloading mechanism (136) is comprised of a biasing device such as a spring (138).

The spring (138) is held between a spring housing (140) and a thrust member (142). The spring housing (140) is connected with the pressure member (128) so that the pressure member (128) is comprised of the spring housing (140).

A first end (144) of the spring (138) is contained within the spring housing (134) and a second end (146) of the spring (138) is carried by the thrust member (142) so that the spring (138) is compressed between the spring housing (140) and the thrust member (142), thereby exerting a preloading engagement force on the fluid line coupler (122). Referring to FIG. 2, in the preferred embodiments the thrust member (142) is a component of the fluid path model frame (43) so that the fluid path model frame (43) is comprised of the thrust member (142).

Referring to FIG. 3, the fluid testing system (20) is further comprised of a source (150) of an electromagnetic radiation which is positioned adjacent to the PVT apparatus (22) and associated with the first viewing window (36) so that electromagnetic radiation may be transmitted through the first viewing window (36) and through the sampling section (48). The fluid testing system (20) is also further comprised of a transmittance sensor (152) which is positioned adjacent to the PVT apparatus (22) and associated with the second viewing window (38) so that transmittance of the electromagnetic radiation through the sampling section (48) may be sensed.

In the preferred embodiments the source (150) of electromagnetic radiation is a source of visible light which is powered by DC power in order to avoid fluctuations in the intensity of the electromagnetic radiation which would result from the use of AC power.

In the preferred embodiments the transmittance sensor (152) is an imaging device which is capable of sensing a spatial distribution of transmittance intensity of the electromagnetic radiation through the sampling section (48).

In the preferred embodiments the imaging device is a camera which is capable of collecting one or more sets of transmittance images. Many different cameras may be suitable for use as the imaging device. The camera used in the preferred embodiments is a thermoelectrically cooled analog PAL video camera. In the preferred embodiments, the camera is coupled with a 10 bit video digitizer (154) for digitizing the transmittance images, which video digitizer (154) provides offset and gain control functionality for controlling the 0 percent and 100 percent range of transmittance intensity in the transmittance images.

An optical filter (not shown) may be attached to the imaging device or otherwise positioned between the source (150) of the electromagnetic radiation and the imaging device in order to control the electromagnetic radiation which is received by the imaging device.

The fluid testing system (20) is also comprised of a memory (160) for storing transmittance images or sets of transmittance images obtained using the camera, and a processor (162) for processing the transmittance images.

The functions of the transmittance sensor (152), the memory (160) and the processor (162) may be separated into different apparatus or combinations of apparatus, or some or all of the functions may be combined into one or more apparatus.

In the preferred embodiments the fluid testing system (20) is used in the performance of the method of the invention. In the preferred embodiments the method of the invention is directed at characterizing an interfacial property of a dispersion using sets of transmittance images, in accordance with FIG. 11 and the first preferred method aspect of the invention. In the preferred embodiments, the method of the invention is also directed at collecting the sets of transmittance images in accordance with the second preferred method aspect of the invention.

In the preferred embodiments of the method the dispersion is comprised of a first fluid (74) and a second fluid (80). The first fluid (74) is a hydrocarbon liquid. The second fluid (80) is a suitable flooding fluid or solvent for the first fluid (74), preferably comprising one or more gases and/or supercritical fluids. For example, a suitable flooding fluid or solvent may be comprised of ethane, propane, carbon dioxide or mixtures thereof. In the preferred embodiments the dispersion may or may not contain solid particles or other fluids.

In the preferred embodiments the interfacial property which is being characterized is a minimum miscibility pressure of the dispersion system comprising the hydrocarbon liquid and the solvent. In the preferred embodiments, the characterization variable is pressure.

The method of the invention may be comprised of observing the behaviour of the dispersion as the characterization variable is varied, since the minimum miscibility pressure will be the pressure at which the interfaces between the first fluid (74) and the second fluid (80) substantially disappear. The observation of the behaviour of the dispersion may be performed directly by watching the dispersion during the performance of the method, or by reviewing sets of transmittance images which are collected during the performance of the method.

The preferred embodiments of the method of the invention, however, involve collecting sets of transmittance images relating to the dispersion and processing the sets of transmittance images in order to determine the minimum miscibility pressure of the dispersion at a particular temperature of the dispersion. As a result, in the preferred embodiments, the pressure of the dispersion is a characterization variable which is varied during the collection of the sets of transmittance images in order to provide transmittance images which may be used to determine the minimum miscibility pressure of the dispersion.

In the preferred embodiments of the method of the invention, the collection of the sets of transmittance images is performed using the fluid testing system (20). Depending upon the configuration of the fluid testing system (20), the processing of the sets of transmittance images may be performed entirely or in part using the fluid testing system (20) or may be performed using other data processing methods and/or apparatus.

The first procedure in the preferred embodiment of the method is providing the fluid path (42). The fluid path (42) may be the long embodiment depicted in FIG. 7, the short embodiment depicted in FIG. 9, or some other configuration of fluid path (42).

The second procedure in the preferred embodiment of the method is introducing an initial amount of the first fluid (i.e., hydrocarbon liquid) (74) into the fluid path (42) so that the hydrocarbon liquid is contained in the fluid path (42). Preferably the fluid path (42) is completely filled with the hydrocarbon liquid.

The third procedure in the preferred embodiment of the method is introducing an amount of the second fluid (i.e., solvent) (80) into the second fluid inlet (68) while maintaining a substantially constant value of the characterization variable (i.e., pressure of the dispersion) in the fluid path (42) in order to displace the hydrocarbon liquid from the fluid path (42) at the outlet end (46) of the fluid path (42). A substantially constant temperature of the dispersion is also maintained during this portion of the method, since minimum miscibility pressure is dependent upon the temperature of the dispersion.

In the preferred embodiments where the interfacial property to be characterized is minimum miscibility pressure, the amount of the second fluid (80) which is introduced into the second fluid inlet (68) is preferably between about 1 time and about 3 times the volume of the fluid path (42). In other applications of the method, the amount of the second fluid (80) which is introduced into the second fluid inlet (68) may vary widely. For example, where the first fluid (74) and the second fluid (80) are immiscible so that the interfacial property is not minimum miscibility pressure, the amount of the second fluid (80) may be as much as about 500 times the volume of the fluid path (42) or more.

The fourth procedure in the preferred embodiment of the method is directing an electromagnetic radiation (i.e., visible light) at the sampling section (48). This procedure is performed by directing the source of light at the first viewing window (36) so that it shines through the first viewing window (36) of the PVT apparatus (22) and thus at the sampling section (48).

Figure 11:
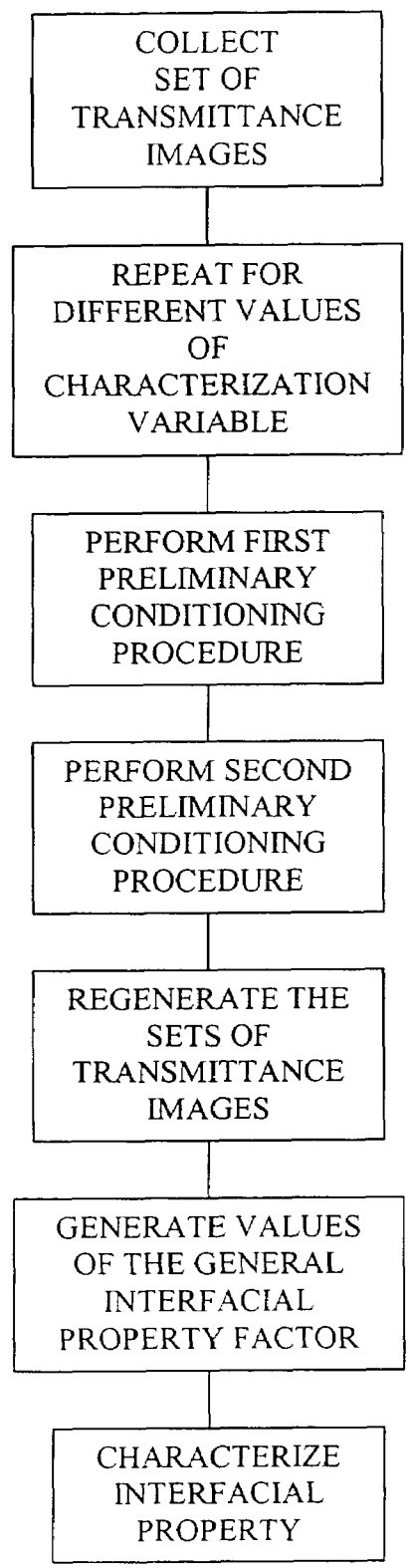
FIG. 11 is a flow chart depicting a preferred embodiment of the first preferred method aspect of the invention.

Referring to FIG. 11, the fifth procedure in the preferred embodiment of the method is collecting a set of transmittance images with the transmittance sensor (152) (i.e., camera) over a sampling time period as the hydrocarbon liquid is displaced from the fluid path (42) by the solvent, wherein each of the transmittance images represents a spatial distribution of transmittance intensity of the light through the sampling section (48) at a sampling time within the sampling time period. The camera is prepared for collecting the transmittance images by selecting an appropriate optical magnification and by setting the dynamic range of the camera to optimize the 0% and 100% transmittance intensity. The collection of the transmittance images is performed by directing the camera at the second viewing window (38) so that the camera collects images of the transmittance of light through the sampling section (48) over the sampling time period. In accordance with the relationships in Beer's Law, the transmittance images will contain information about the dispersion and its constituents, which information may be used to characterize the interfacial property of the dispersion.

Referring to FIG. 11, the sixth procedure in the preferred embodiment of the method is repeating the above procedures one or more times at different pressures of the dispersion in order to collect a plurality of sets of transmittance images, wherein each set of transmittance images is collected at a different pressure of the dispersion.

Referring to FIG. 11, the seventh procedure in the preferred embodiment of the method is processing the sets of transmittance images in order to characterize the interfacial property of the dispersion (i.e., determine the minimum miscibility pressure of the dispersion). In the preferred embodiments, processing the sets of transmittance images involves performing preliminary conditioning procedures on the transmittance images, generating a value of a general interfacial property factor from each of the sets of transmittance images, and determining the minimum miscibility pressure using the values of the general interfacial property factor.

Referring to FIG. 11, in the preferred embodiments, the sets of transmittance images are subjected to two preliminary conditioning procedures after they are collected.

In a first preliminary conditioning procedure, each of the transmittance images is processed to provide an intensity spatial correction of the transmittance images in order to account for variations in a spatial distribution of intensity of the electromagnetic radiation being directed at the sampling section (48) (See Russ, John C., *The Image Processing Handbook*, 4$^{th}$ Edition, CRC, 2002).

In the first preliminary conditioning procedure, a background transmittance image is collected, wherein the background transmittance image represents a spatial distribution of transmittance intensity of the electromagnetic radiation through the sampling section (48) without the influence of the hydrocarbon liquid or the solvent in the sampling section (48). The background transmittance image is then used to correct each of the transmittance images to provide the intensity spatial correction.

The background transmittance image may be collected before the hydrocarbon liquid is introduced into the fluid path (42), in which case the background transmittance image may be collected simply by directing the light through the sampling section (48) and collecting the background transmittance image with the camera.

In the preferred embodiments, however, the background transmittance image may be collected after the hydrocarbon liquid and/or the solvent are introduced into the fluid path (42) by directing the light through the sampling section (48), selectively sensing the transmittance of the light to eliminate the influence of the hydrocarbon liquid and/or the solvent, and interpolating the selectively sensed transmittance in order to collect the background transmittance image.

More particularly, and referring to FIGS. 7-10, the fluid path (42) within the sampling section (48) includes the protrusions which make up the arrangement of obstructions (62). The sampling section (48) may also include portions of the transparent layers (50,52) which are not comprised of the fluid path (42). These protrusions and transparent layers (50,52) are essentially transparent, with the result that transmittance of light through the protrusions and transparent layers (50,52) is not dependent upon whether a fluid is present in the fluid path (42).

As a result, the background transmittance image may be collected by directing the light through the sampling section (48), sensing the transmittance of light through only the obstructions (62) and portions of the transparent layers (50,52) which are not comprised of the fluid path (42), and interpolating the sensed transmittance of light in order to collect the background transmittance image. The transmittance of light may be selectively sensed by determining which pixels of the camera image correspond with the obstructions (62 and portions of the transparent layers (50,52), and then using only those pixels to collect the background transmittance image.

In the preferred embodiments the interpolation is performed by fitting the transmittance of light at the selected pixels with a three-dimensional polynomial using a multi-dimensional least squares method according to the following general formula:

$$z = a_0 + a_1 x + a_2 y + a_3 x^2 + a_4 y^2 + a_5 xy$$

where:

z=transmittance intensity a=least squares coefficients

The resulting function is then used to calculate the transmittance intensity for all of the pixels in the background transmittance image, thus interpolating the transmittance of light which is sensed at the selected pixels.

The background transmittance image may then be used to correct the transmittance images in any manner which will provide the intensity spatial correction. For example, the background transmittance image may be subtracted from or divided into the transmittance images. In the preferred embodiments the background transmittance image is divided into the transmittance images in order to normalize the transmittance images in accordance with Beer's Law and thus provide the intensity spatial correction.

In a second preliminary conditioning procedure, each of the transmittance images is processed to provide an intensity time correction of the transmittance images in order to account for variations over time in the intensity of the electromagnetic radiation being directed at the sampling section (48).

In the second preliminary conditioning procedure, a histogram is produced representing each of the transmittance images, wherein each of the histograms provides a relationship between transmittance intensity and frequency of transmittance intensity throughout the transmittance image at one of the sampling times. The histograms are then processed to provide the intensity spatial correction.

The first procedure in processing the histograms is to produce cumulative frequency distributions for each of the histograms. The cumulative frequency distributions are then processed below a lower cumulative frequency threshold and above an upper cumulative frequency threshold. In the preferred embodiments the lower cumulative frequency threshold is selected to be one (1%) percent and the upper cumulative frequency threshold is selected to be ninety-nine (99%) percent.

More specifically, a lower limit transmittance intensity is determined for each of the cumulative frequency distributions at the lower cumulative frequency threshold and any transmittance intensities below the lower limit transmittance intensity are adjusted to the lower limit transmittance intensity. Similarly, an upper limit transmittance intensity is determined for each of the cumulative frequency distributions at the upper cumulative frequency threshold and any transmittance intensities above the upper limit transmittance intensity are adjusted to the upper limit transmittance intensity. Once the adjustments to the transmittance intensities have been made, the transmittance images are regenerated using the adjusted transmittance intensities so that the regenerated transmittance images include the intensity time correction.

Once the preliminary conditioning procedures have been performed on the transmittance images, the sets of transmittance images are processed to generate the values of the general interfacial property factor.

The general interfacial property factor may be any variable or characteristic which yields a value from a set of transmittance images such that the values of the general interfacial property factor obtained from a plurality of sets of transmittance images may be used to characterize the interfacial property of the dispersion. The nature of the general interfacial property factor depends upon how the transmittance images are processed to generate the values of the general interfacial property factor.

In the preferred embodiments, the values of the general interfacial property factor are generated using a preferred embodiment of either a Image Histogram Method, a Direct Frequency Domain Method, or a Derivative Image Frequency Domain Method. In each of these three methods, the general interfacial property factor represents a different property of the sets of transmittance images.

Figure 12A:
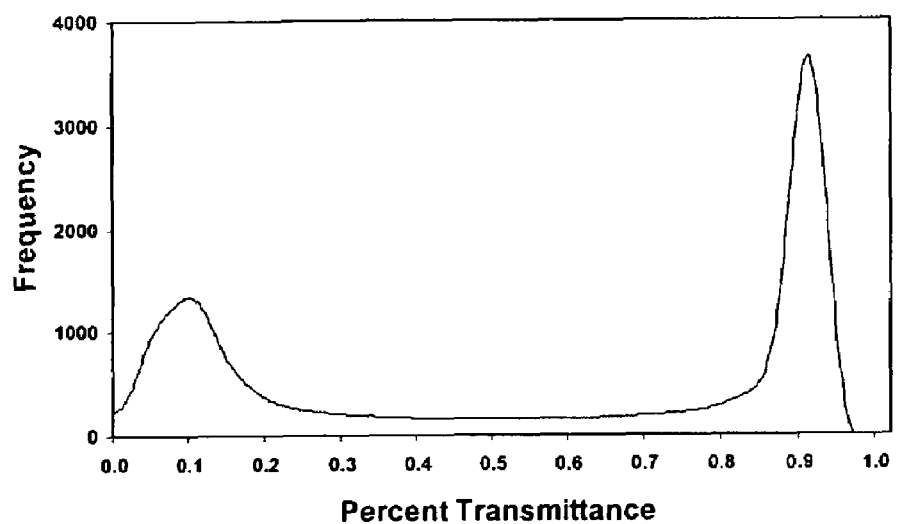
Figure 12B:
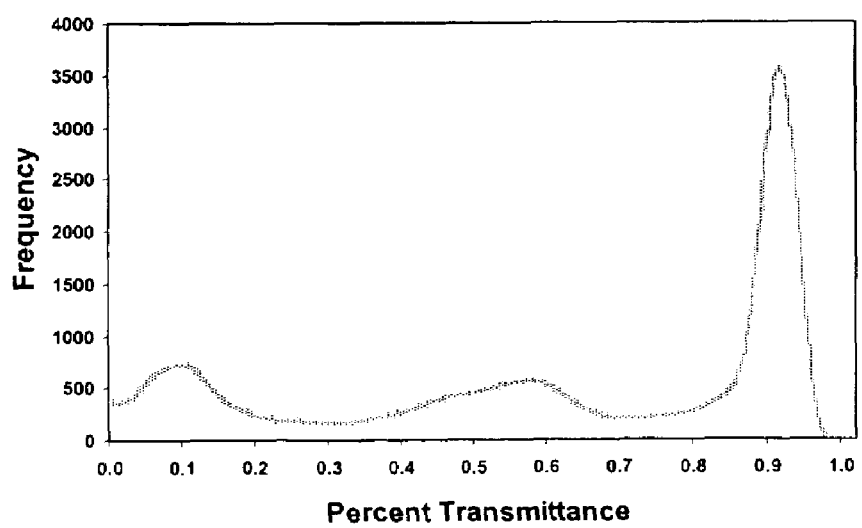
Figure 12C:
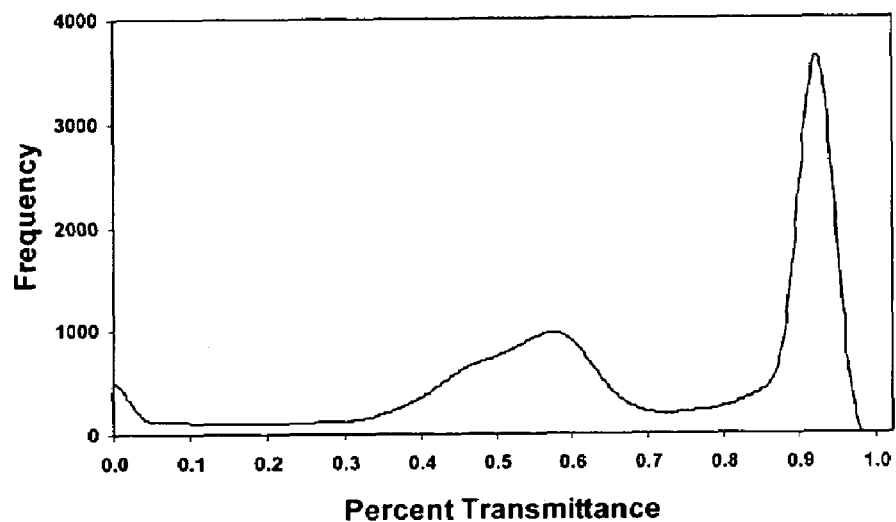
Figure 13:
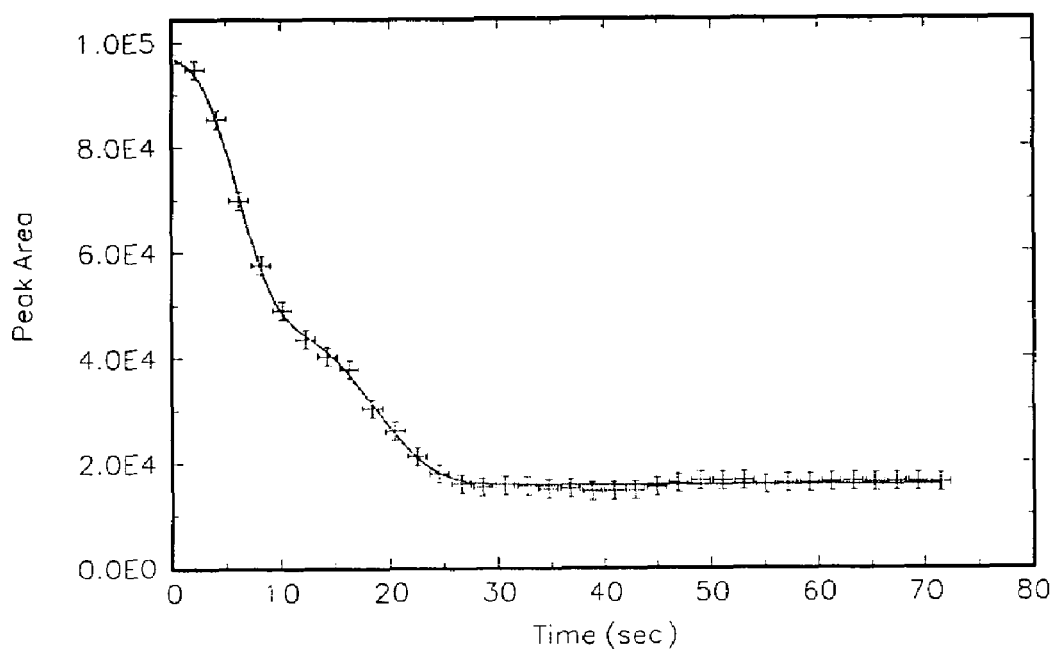
FIG. 13 is an exemplary graph as would be produced in the Image Histogram Method of the invention, depicting a first relationship between peak area of a hydrocarbon liquid and sampling time.
Figure 14:
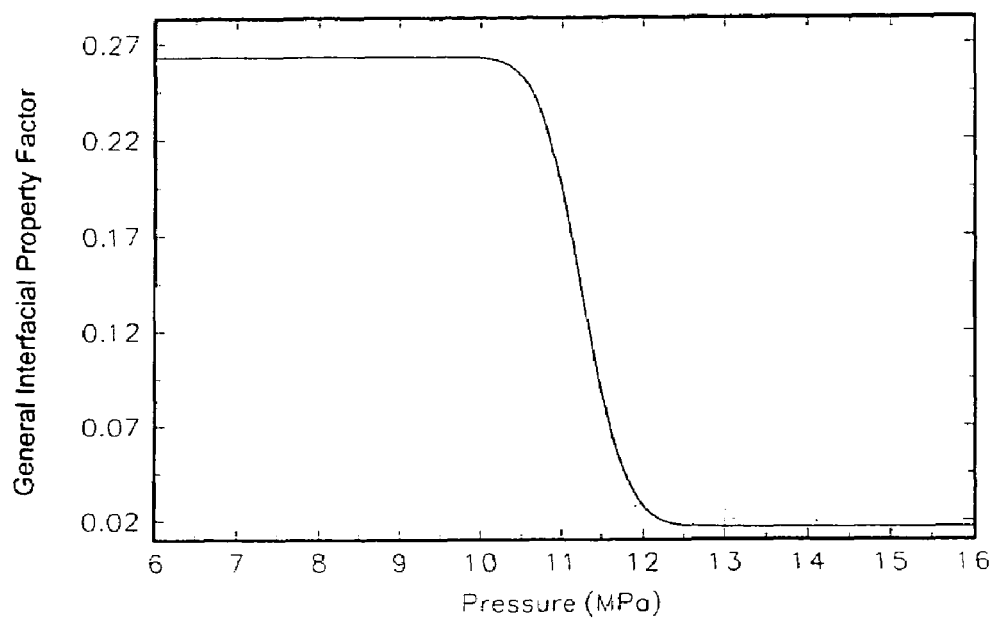
FIG. 14 is an exemplary graph as would be produced in the Image Histogram Method of the invention, depicting a second relationship between general interfacial property factor and pressure.

Referring to FIGS. 12-14, in the Image Histogram Method a value of the general interfacial property factor for a set of transmittance images may be generated as follows.

The graphs depicted in FIGS. 12-14 are exemplary of relationships which may be expected for transmittance images collected using a short embodiment of a fluid path (42) such as the fluid path (42) depicted in FIGS. 9-10. In FIGS. 12-14, the first fluid (74) is a hydrocarbon liquid and the second fluid (80) is ethane.

First, referring to FIG. 12(*a*), FIG. 12(*b*) and FIG. 12(*c*), a histogram is produced representing each transmittance image in a set of transmittance images, wherein each of the histograms provides a frequency relationship between transmittance intensity and frequency of transmittance intensity throughout the transmittance image at one of the sampling times.

Second, a first peak and a second peak are identified from each of the histograms. The first peak represents transmittance intensity of the electromagnetic radiation through the hydrocarbon liquid and the second peak represents transmittance intensity of the electromagnetic radiation through the solvent. A third peak representing transmittance intensity of the electromagnetic radiation through the portions of the transparent layers (50,52) which do not include the fluid path (42) is ignored.

Third, a first peak area is calculated for each of the first peaks and/or a second peak area is calculated for each of the second peaks. The first peak area represents an amount of the hydrocarbon liquid in the transmittance image and the second peak area represents an amount of the solvent in the transmittance image.

Fourth, referring to FIG. 13, a first relationship is determined using the first peak areas and/or the second peak areas and the sampling times. The first relationship may be determined with reference to either the first peak areas or the second peak areas so that the first relationship is expressed as a peak area as a function of sampling time. The first relationship may also be determined from both the first peak areas and the second peak areas so that the first relationship is expressed as a peak area ratio of the first peak area to the second peak area as a function of sampling time. In the preferred embodiments the first relationship is expressed as first peak area as a function of sampling time. The first relationship may be expressed mathematically or graphically. Actual sampling times or normalized sampling times may be used to express the first relationship.

Fifth, the first relationship is used to determine the value of the general interfacial property factor. Referring to FIG. 13, a curve depicting a fit of raw data points from a first relationship for the Image Histogram Method is depicted. The curve may be fit to the raw data points using any suitable curve fitting technique. In the preferred embodiments of the Histogram Method the curve is fit to the raw data points using a non-linear least squares model according to the following general equation:

$$y = \sum_{i=1}^{n}\left[\frac{\sqrt{2}\sqrt{\pi}\cdot H_i\sigma_i\text{erf}\left[\frac{\sqrt{2}(m_i - x)}{2\sigma_i}\right]}{2}\right] + C$$

where:
H=the maximum value of y
m=the mean value of an associated Gaussian curve
σ=is standard deviation
C=is a constant
n=the number of curves making up the function As can be seen from FIG. 13, the value of the first peak area approaches a relatively stable value toward the end of the sampling time period. This relatively stable value effectively represents a residual (unmixed) amount of the hydrocarbon liquid in the dispersion for the pressure at which the set of transmittance images was collected.

This relatively stable value may be described as an "endpoint first peak area". In the preferred embodiments this endpoint first peak area is used as the value of the general interfacial property factor for the pressure at which the set of transmittance images was collected.

Depending upon the characteristics of the first relationship, the endpoint first peak area may be difficult to discern from the first relationship.

As a result, alternatively some other quantity derived from the first relationship and representative of the interfacial property to be characterized may be used as the value of the general interfacial property factor. In such circumstances, it may not be necessary to fit a curve to the raw data points representing the first relationship in the manner as described above, since the raw data points may possibly be used directly to identify the value of the general interfacial property factor.

The preceding five procedures are repeated for each set of transmittance images in order to generate a plurality of values of the endpoint first peak area as a function of the pressures at which the sets of transmittance images were collected.

Referring to FIGS. 15-28, in the Direct Frequency Domain Method values of the general interfacial property factor for sets of transmittance image are generated as follows.

The graphs depicted in FIGS. 15-28 are exemplary of relationships which may be expected for transmittance images collected using a short embodiment of a fluid path (42) such as the fluid path (42) depicted in FIGS. 9-10. In FIGS. 15-28, the first fluid (74) is a hydrocarbon liquid and the second fluid (80) is ethane.

Figure 15:
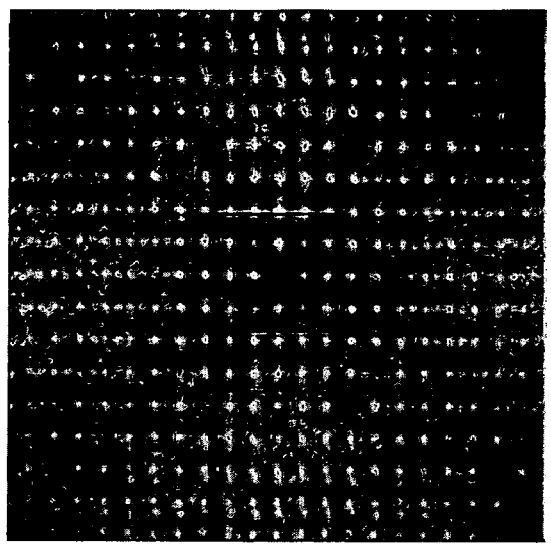
FIG. 15 is an exemplary transformed transmittance image from a short embodiment of a fluid path as would be produced in the Direct Frequency Domain Method, including a representation of the frequency region of interest.

First, referring to FIG. 15, each of the transmittance images in a set of transmittance images is transformed into a frequency domain to produce a transformed transmittance image, wherein each of the transformed transmittance images provides a frequency relationship between transmittance intensity and frequency of transmittance intensity throughout the transmittance image at one of the sampling times. In other words, each of the transformed transmittance images represents a two-dimensional frequency domain power spectrum.

The transmittance images may be transformed into the frequency domain in any manner. For example, the transmittance images may be transformed using such methods as the Fourier transform (FT) method, Fast Fourier transform (FFT) method, maximum entropy method, free cosine transform method, discrete cosine transform method and wavelet analysis method. In the preferred embodiments the transmittance images are transformed using the Fast Fourier transform method.

Second, referring to FIG. 15, a frequency region of interest is identified in each of the transformed transmittance images. The identification of the frequency region of interest may be dependent upon the composition of the dispersion, upon the characterization variable and upon the interfacial property which is being characterized. The frequency region of interest may be any shape. Referring to FIG. 15, in the preferred embodiments the frequency region of interest is circular or square.

In the preferred embodiments where the interfacial property is minimum miscibility pressure, the frequency region of interest consists of relatively low frequencies between zero and an upper frequency limit.

In the preferred embodiments the upper frequency limit is selected so that the ratio in each transformed transmittance image between the area of the frequency region of interest and the area of the transformed transmittance image is no greater than about 0.25:1 and more preferably is no greater than about 0.1:1. The frequency region of interest is the same for each of the transformed transmittance images.

Third, a frequency region integral is calculated for the frequency region of interest of each of the transformed transmittance images. The frequency region integral is calculated by integrating the frequency region of interest in two dimensions. The frequency region integral represents the influence of interfaces between the hydrocarbon liquid and the solvent in the dispersion.

Figure 16:
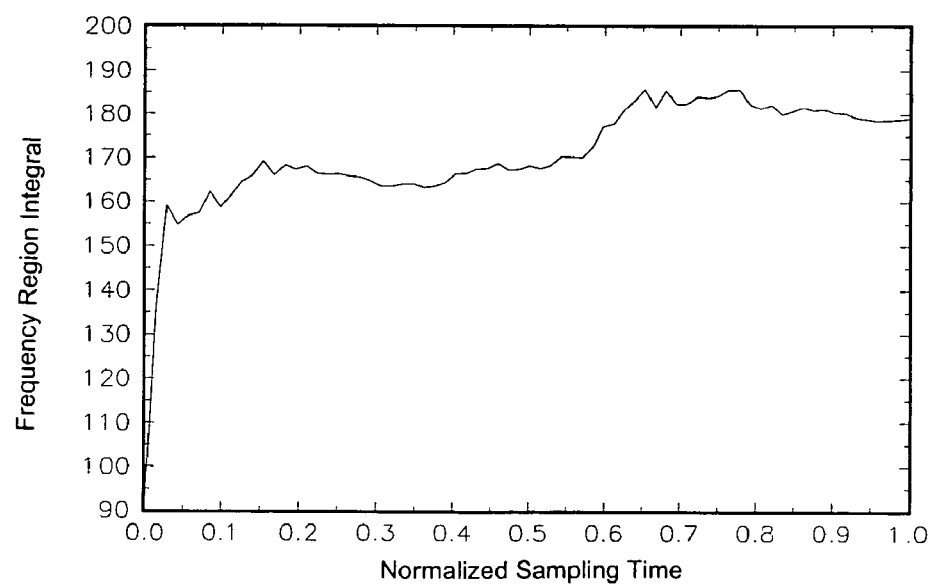
FIGS. 16-27 are exemplary graphs as would be produced in the Direct Frequency Domain Method of the invention using a short embodiment of a fluid path, each depicting a first relationship between frequency region integral and normalized sampling time for different values of pressure as the characterization variable.
Figure 17:
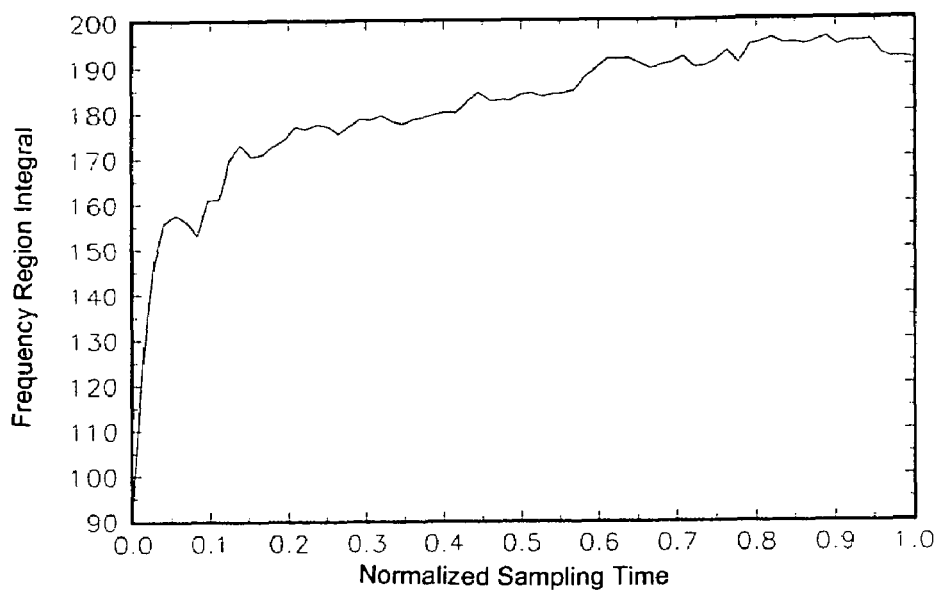
Figure 18:
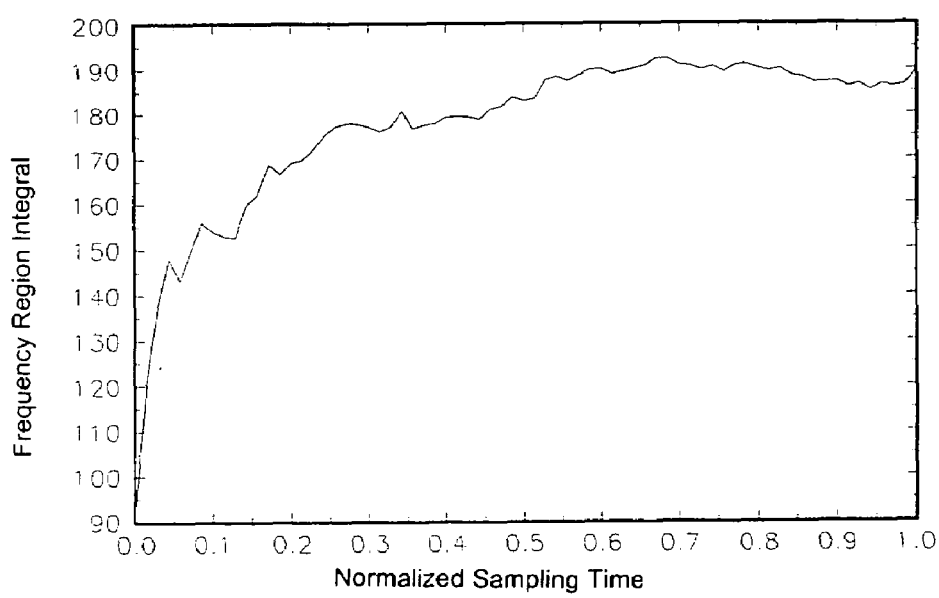
Figure 19:
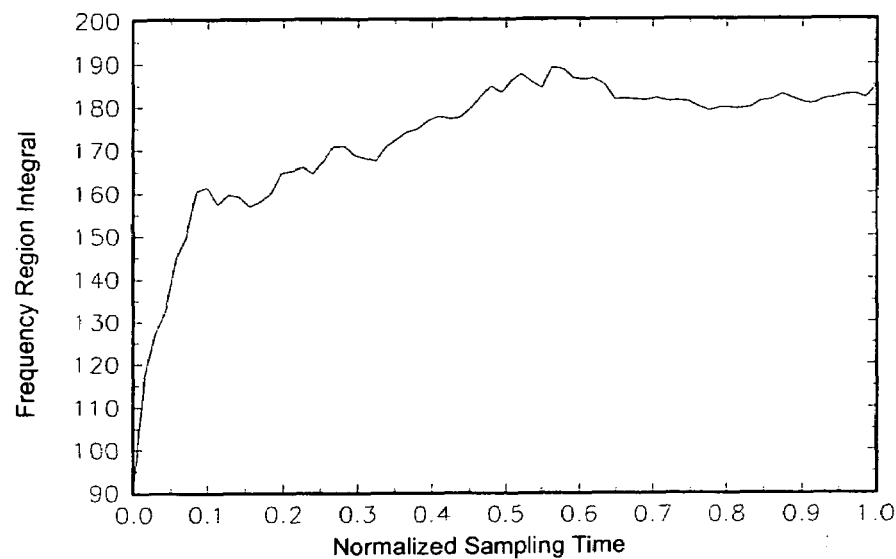
Figure 20:
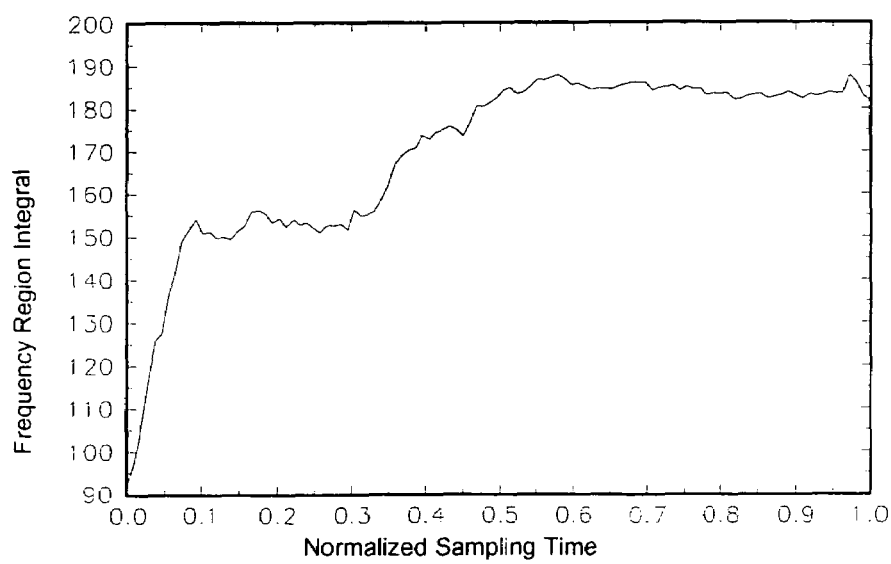
Figure 21:
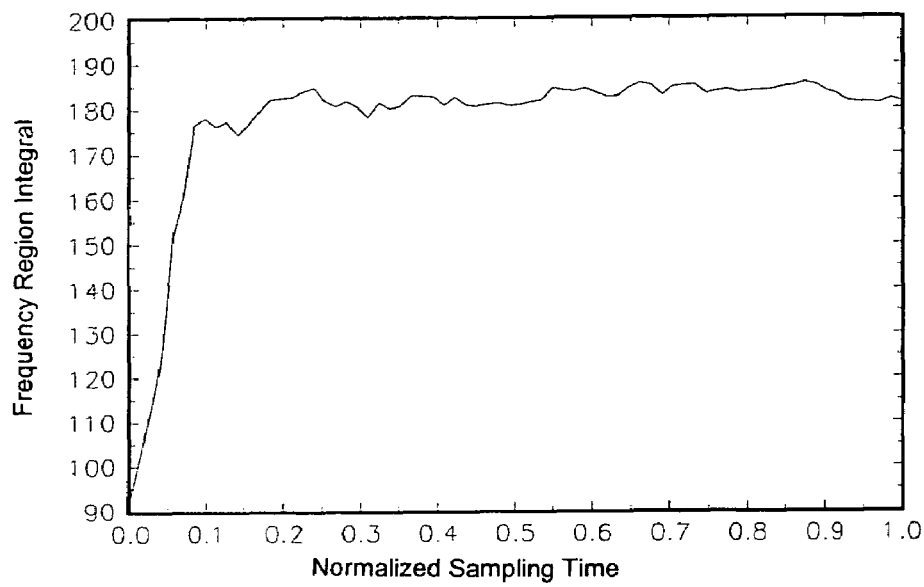
Figure 22:
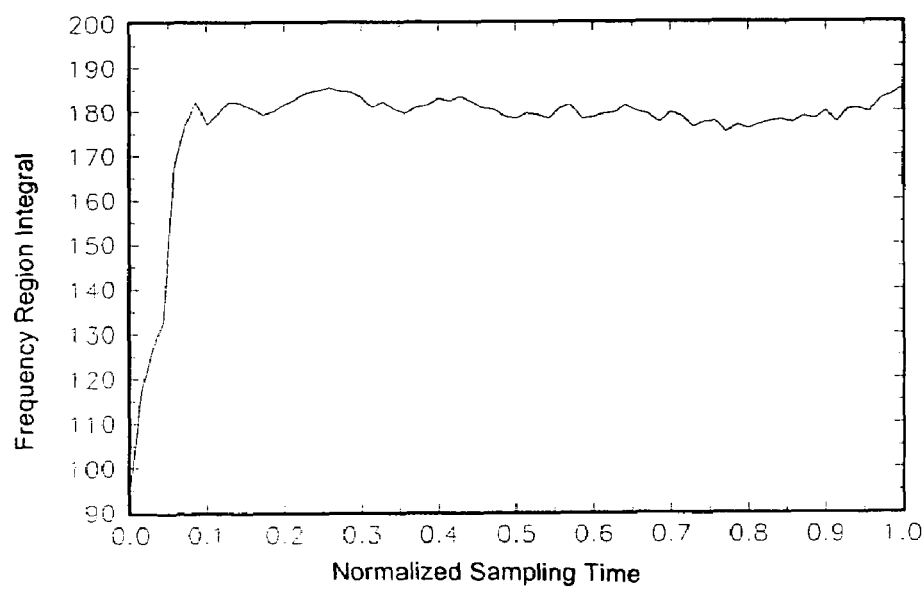
Figure 23:
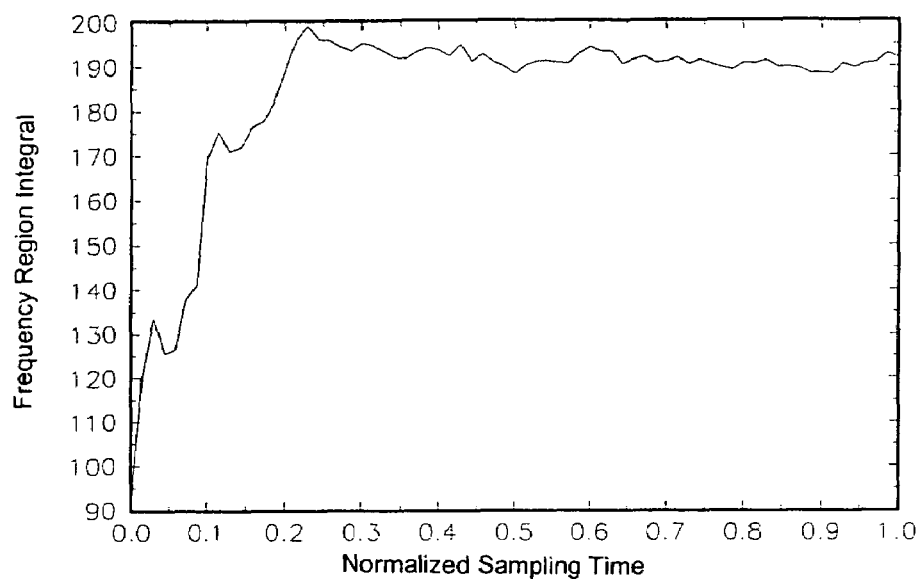
Figure 24:
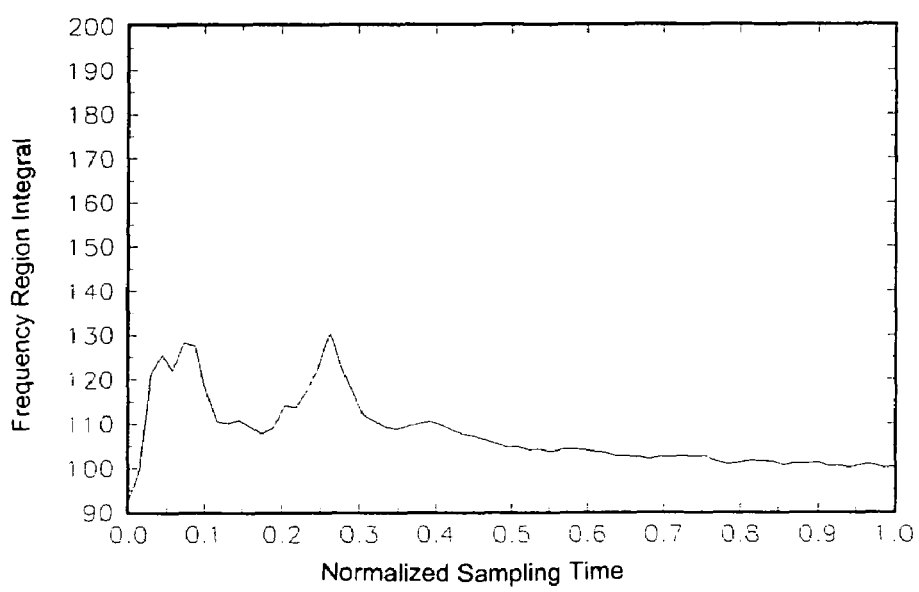
Figure 25:
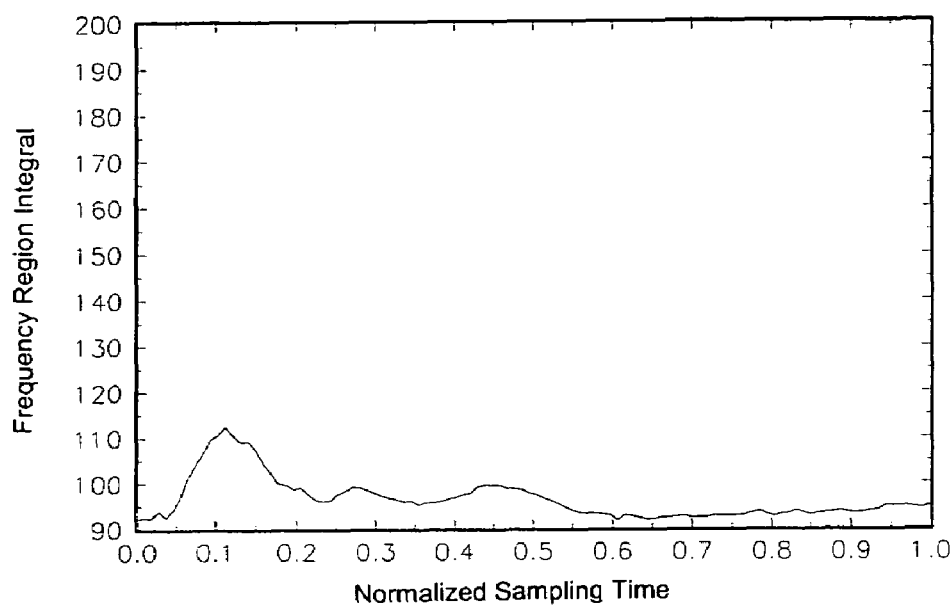
Figure 26:
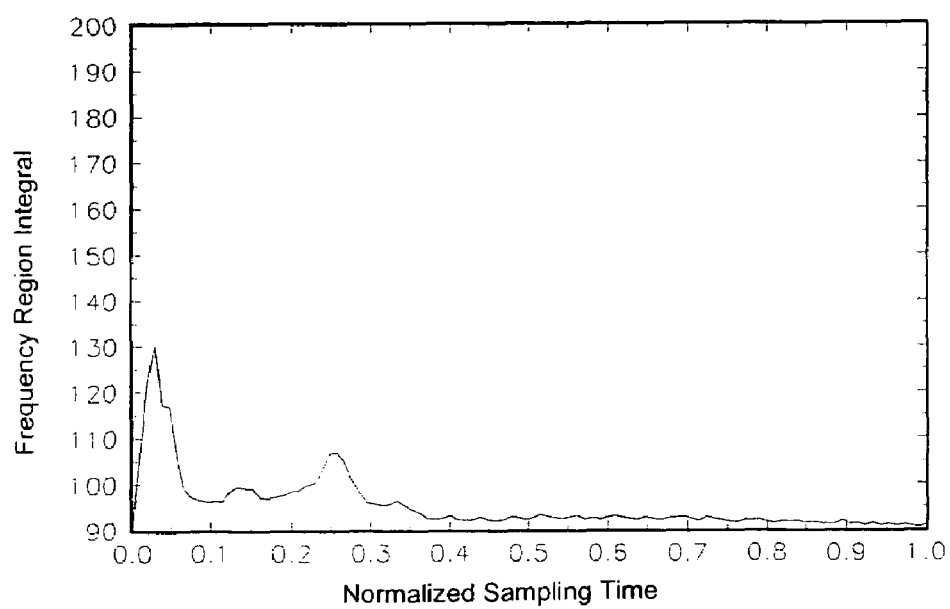
Figure 27:
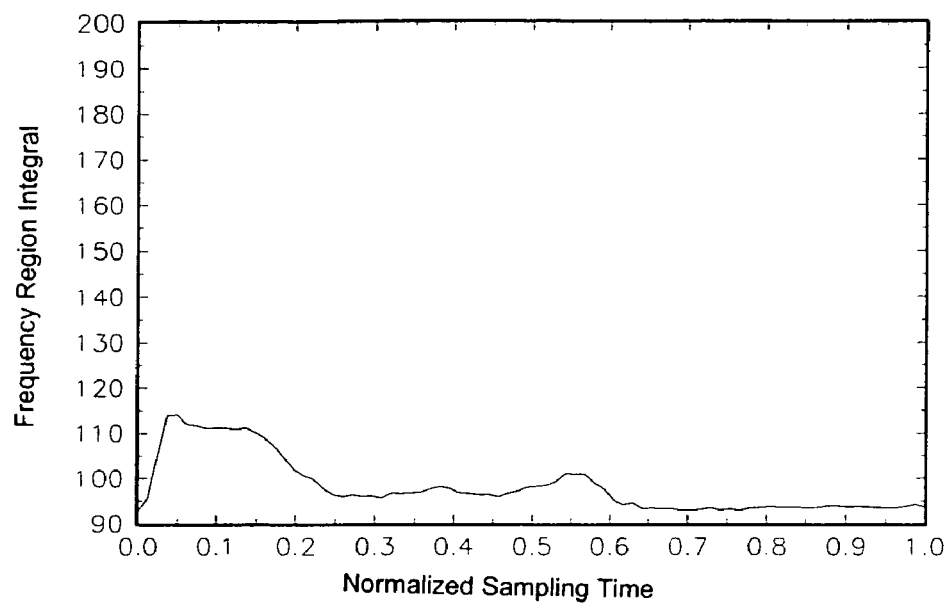

Fourth, referring to FIG. 16, a first relationship is determined between the frequency region integrals calculated from the transformed transmittance images and the sampling times. The first relationship may be expressed mathematically or graphically. Actual sampling times or normalized sampling times may be used to express the first relationship.

Fifth, the first relationship is used to determine the value of the general interfacial property factor. Referring to FIG. 16, a curve depicting a fit of raw data points from a first relationship at a pressure of 6.0 MPa for the Direct Frequency Domain Method is depicted. The curve may be fit to the raw data points using any suitable curve fitting technique. In the preferred embodiments of the Direct Frequency Domain Method the curve may be fit to the raw data points using the same non-linear least squares model which is described for the Image Histogram Method.

As can be seen from FIG. 16, the value of the frequency region integral approaches a relatively stable value toward the end of the sampling time period. This relatively stable value effectively represents the interfaces between the hydrocarbon liquid and the solvent as the dispersion stabilizes at the pressure at which the set of transmittance images was collected.

This relatively stable value may be described as an "endpoint frequency region integral". In the preferred embodiments this endpoint frequency region integral is used as the value of the general interfacial property factor for the pressure at which the set of transmittance images was collected.

Depending upon the characteristics of the first relationship, the endpoint frequency region integral may be difficult to discern from the first relationship.

As a result, alternatively the value of the general interfacial property factor may be an average frequency region integral which is identified from the first relationship, an integral of the first relationship, or some other quantity which is derived from the first relationship and which is representative of the interfacial property to be characterized. In such circumstances, it may not be necessary to fit a curve to the raw data points representing the first relationship, since the raw data points may possibly be used directly to identify the value of the general interfacial property factor.

Referring to FIGS. 17-27, the preceding five procedures are repeated for each set of transmittance images in order to generate a plurality of values of the endpoint frequency region integral as a function of the pressures at which the sets of transmittance images were collected.

Referring to FIGS. 29-40, in the Derivative Image Frequency Domain Method values of the general interfacial property factor for sets of transmittance images are generated as follows.

The graphs depicted in FIGS. 29-40 are exemplary of relationships which may be expected for transmittance images collected using a short embodiment of a fluid path (42) such as the fluid path (42) depicted in FIGS. 9-10. In FIGS. 29-40, the first fluid (74) is a hydrocarbon liquid and the second fluid (80) is ethane.

As a preliminary procedure, the set of transmittance images is processed to produce a set of derivative transmittance images, wherein each of the derivative transmittance images represents a spatial distribution of a difference in transmittance intensity of the electromagnetic radiation between a pair of the transmittance images collected at a pair of the sampling times. In other words, a derivative transmittance image represents a slope or derivative of transmittance intensity as a function of time.

More particularly, the derivative transmittance images are produced according to the following formulae:

$$\frac{di}{dt} = \frac{\partial i}{\partial x}\frac{\partial x}{\partial t} + \frac{\partial i}{\partial y}\frac{\partial y}{\partial t}$$

(as a continuous function)

$$\frac{\Delta i}{\Delta t} = \frac{\Delta i}{\Delta x}\frac{\Delta x}{\Delta t} + \frac{\Delta i}{\Delta y}\frac{\Delta y}{\Delta t}$$

(as a discrete function)
Where:
i=transmittance intensity
t=time interval between sampling times for a pair of transmittance images
x=horizontal direction in the transmittance images
y=vertical direction in the transmittance images In the preferred embodiments, the derivative transmittance images may be further processed to eliminate negative numbers by adjusting upward the range of the "differences in transmittance intensity". For example, if the range of transmittance intensity in the transmittance images is between 0 and 100, then the range of differences in transmittance intensity in the derivative transmittance images is between −100 and 100. The range of the differences in transmittance intensity may therefore be adjusted upward so that the range of differences in transmittance intensity which are used in the derivative transmittance images is between 0 and 200.

Once the derivative transmittance images are produced, the values of the general interfacial property factor may be generated in a similar manner as in the Direct Frequency Domain Method. However, in the preferred embodiments of the Derivative Image Frequency Domain Method, the values of the general interfacial property factor are generated in a slightly different manner than in the preferred embodiments of the Direct Frequency Domain Method.

First, each derivative transmittance image is transformed into a frequency domain to produce a transformed derivative transmittance image, wherein each of the transformed derivative transmittance images provides a frequency relationship between difference in transmittance intensity and frequency of the difference in transmittance intensity throughout the derivative transmittance image during the time interval defined by the pair of sampling times.

The derivative transmittance images may be transformed into the frequency domain using the same methods used in the Direct Frequency Domain Method.

Second, a frequency region of interest is identified in each of the transformed derivative transmittance images. The frequency region of interest may be identified in the same manner as in the Direct Frequency Domain Method.

Third, a frequency region integral is calculated for the frequency region of interest of each of the transformed derivative transmittance images.

Fourth, a first relationship is determined between the frequency region integrals calculated from the transformed derivative transmittance images and the sampling times. The first relationship may be expressed mathematically or graphically. Actual sampling times or normalized sampling times may be used to express the first relationship.

Figure 29:
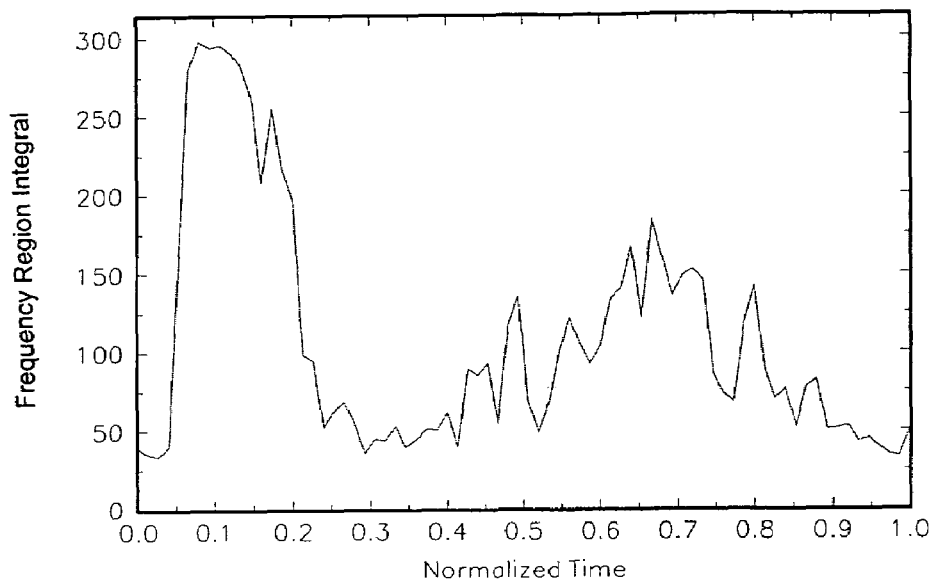
FIGS. 29-40 are exemplary graphs as would be produced in the Derivative Image Frequency Domain Method of the invention using a short embodiment of a fluid path, each depicting a first relationship between frequency region integral and normalized sampling time for different values of pressure as the characterization variable.
Figure 30:
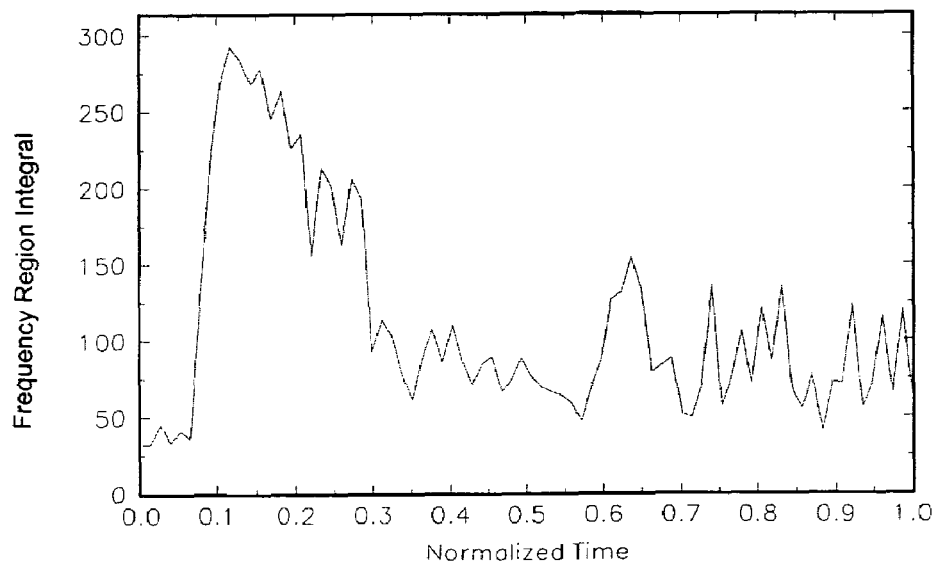
Figure 31:
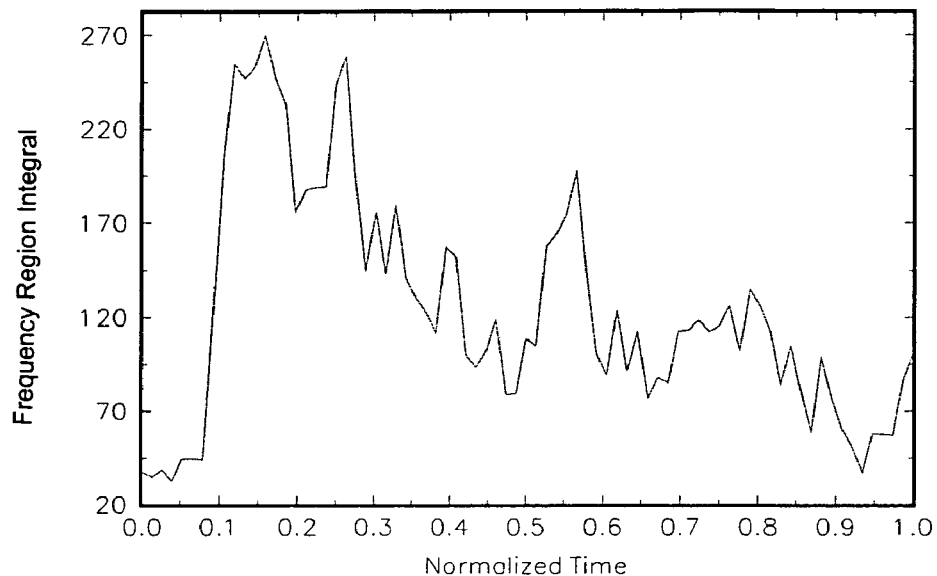
Figure 32:
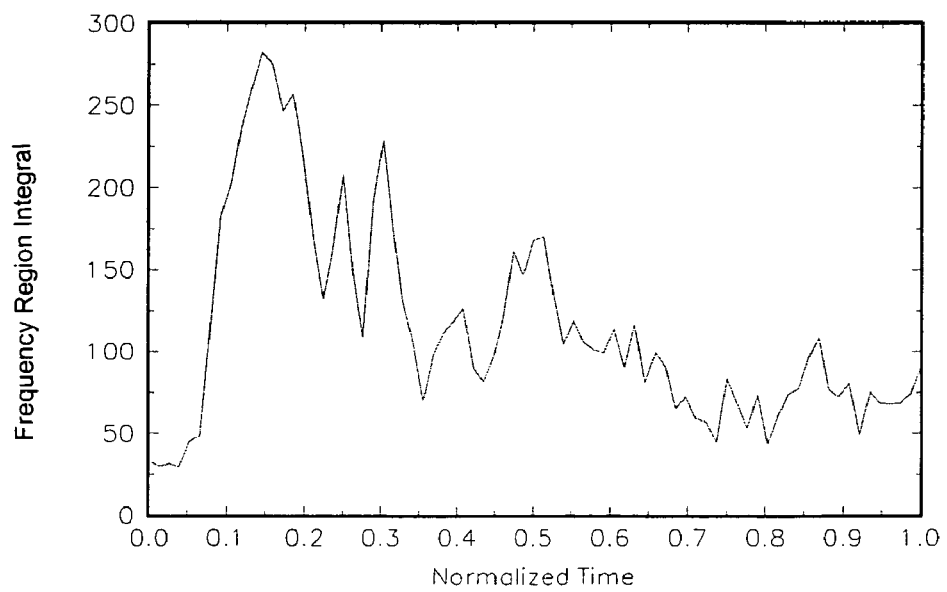
Figure 33:
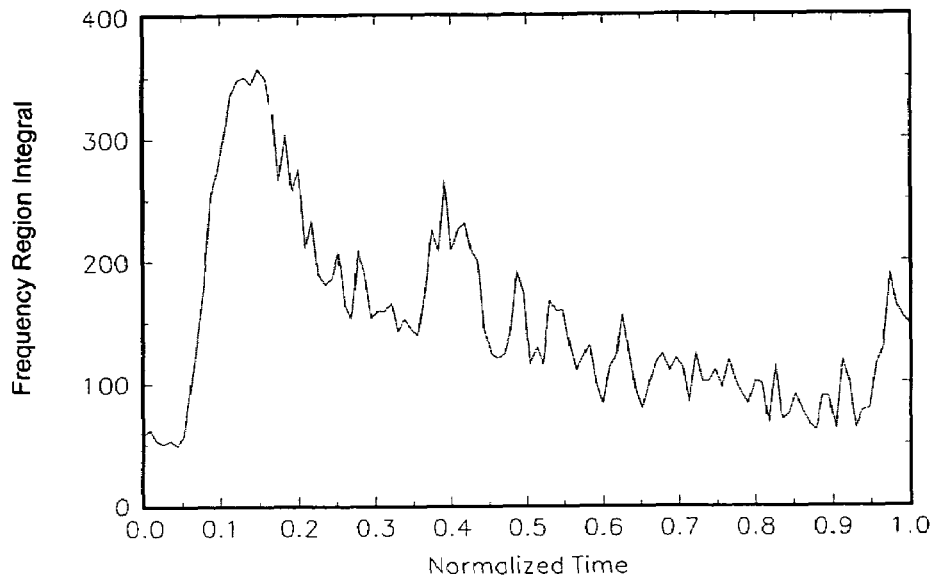
Figure 34:
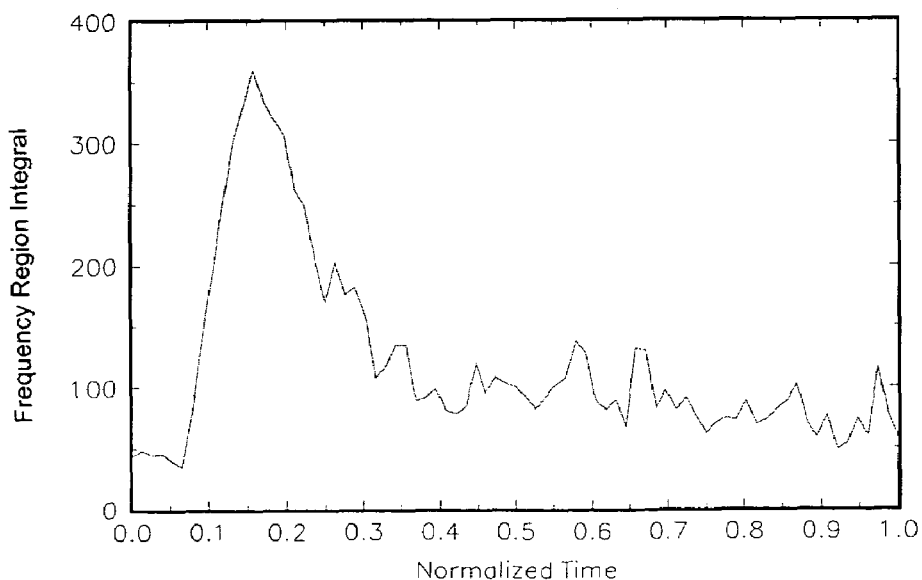
Figure 35:
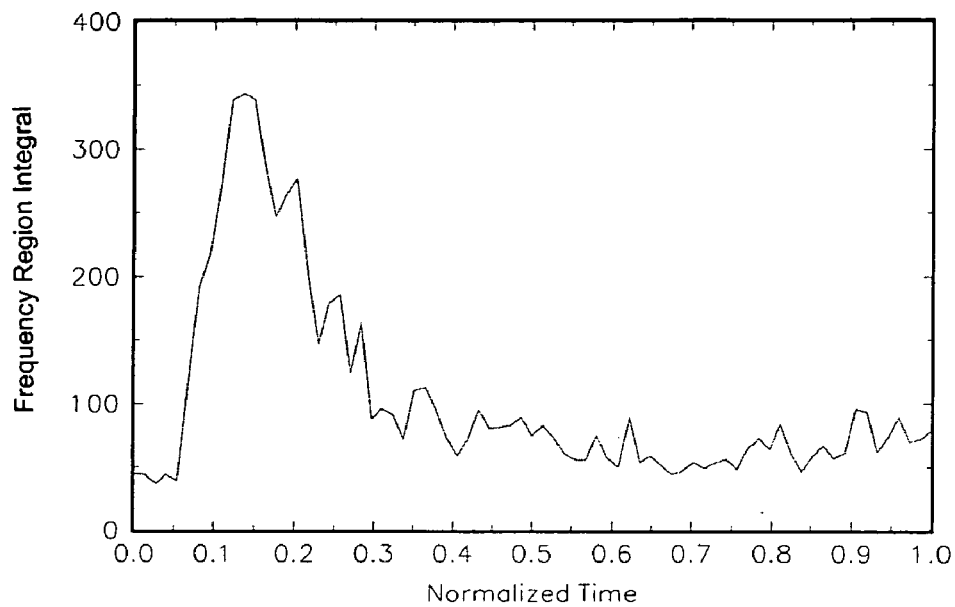
Figure 36:
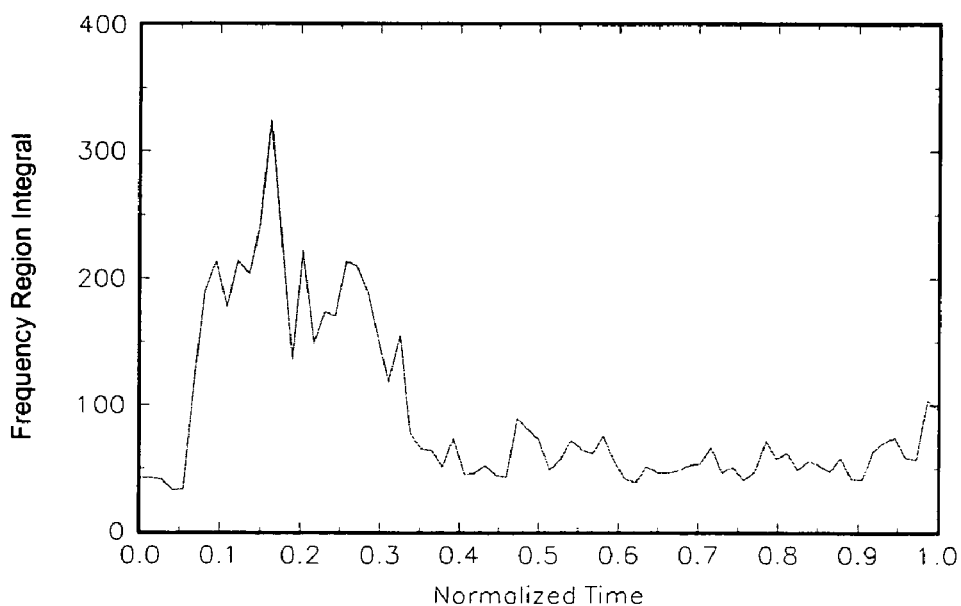
Figure 37:
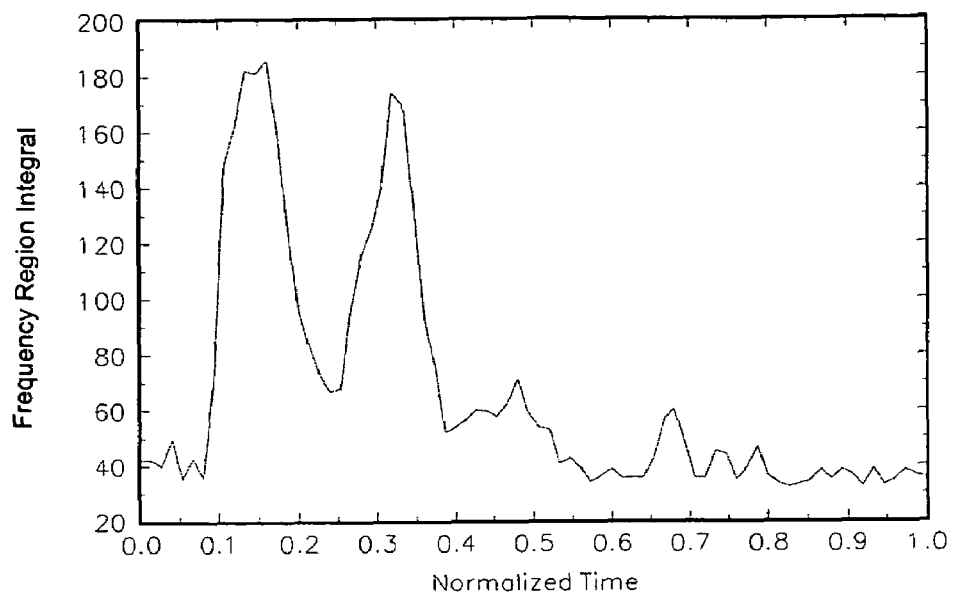
Figure 38:
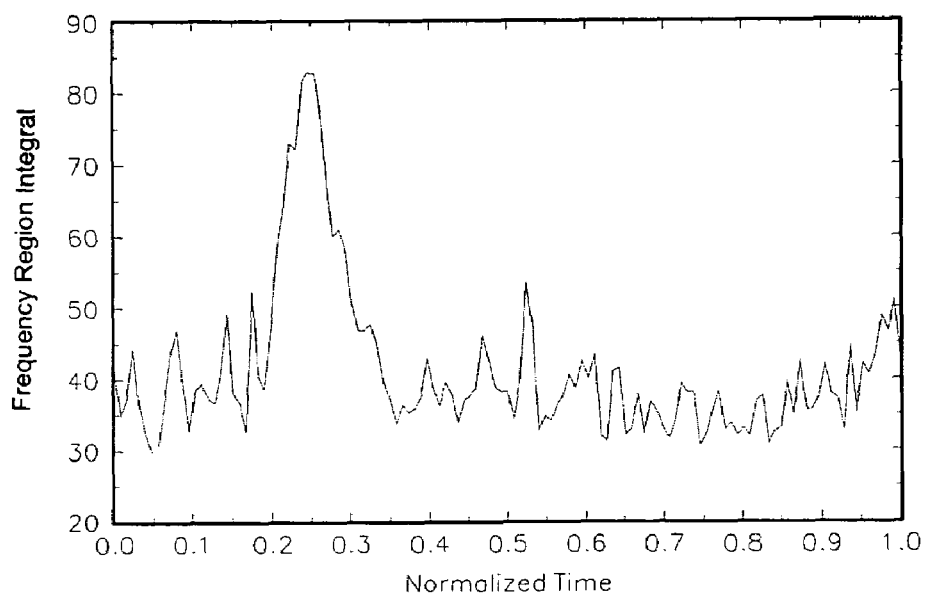
Figure 39:
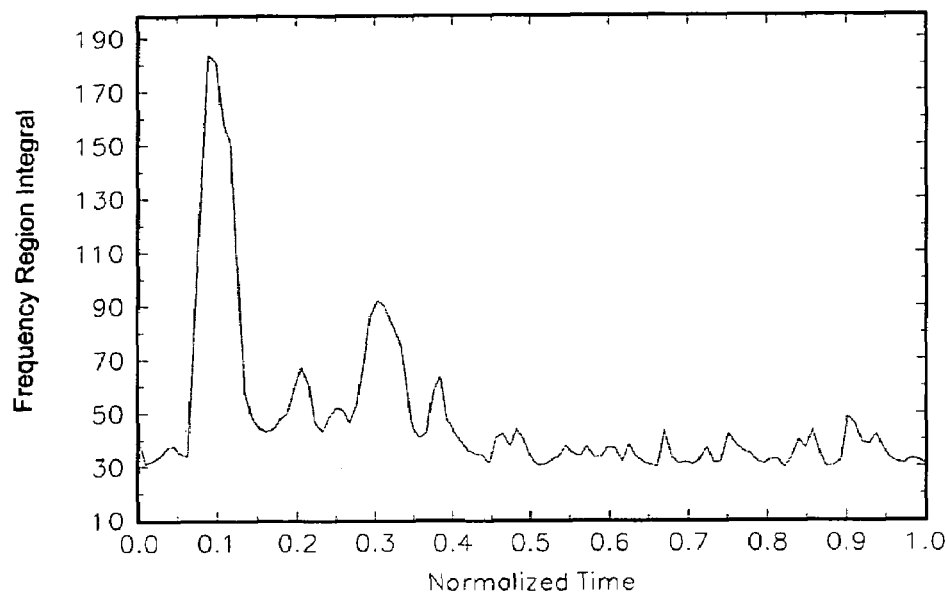
Figure 40:
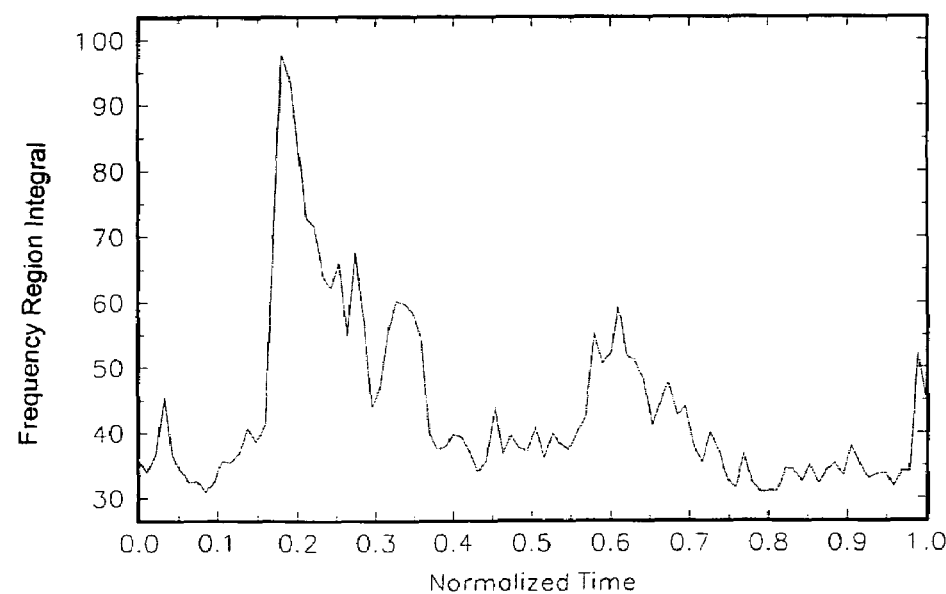

Fifth, the first relationship is used to determine the value of the general interfacial property factor. Referring to FIG. 29, a plot of raw data points representing a first relationship at a pressure of 6.0 MPa for the Derivative Image Frequency Domain Method is depicted. In the preferred embodiments of the Derivative Image Frequency Domain Method the raw data points are not fit to a curve as in the Direct Frequency Domain Method, but are plotted directly. Alternatively, a curve may be fit to the raw data points using a suitable curve fitting technique, but curve fitting is an unnecessary procedure in the preferred embodiments of the Derivative Image Frequency Domain Method having regard to the manner in which the general interfacial property factor is identified from the first relationship, as discussed below.

As can be seen from FIG. 29, the value of the frequency region integral fluctuates widely during the sampling time period and does not approach a stable value as was observed in FIGS. 16-27 for the Direct Frequency Domain Method. As a result, an "endpoint frequency region integral" may not be readily identified from FIG. 29.

Consequently, the value of the general interfacial property factor may be an average frequency region integral which is identified from the first relationship, an integral of the first relationship, or some other quantity which is derived from the first relationship and which is representative of the interfacial property to be characterized.

In the preferred embodiments of the Derivative Image Frequency Domain Method, an integral of the first relationship is used as the value of the general interfacial property factor for the pressure at which the set of transmittance images was collected. The use of the integral of the first relationship as the value of the general interfacial property factor renders unnecessary the procedure of using a curve fitting technique to fit a curve to the raw data points, since the raw data points may be used directly to calculate the integral of the first relationship.

Referring to FIGS. 30-40, the preceding five procedures are repeated for each set of transmittance images in order to generate a plurality of values of the integral of the first relationship as a function of the pressures at which the sets of transmittance images were collected.

Figure 42:
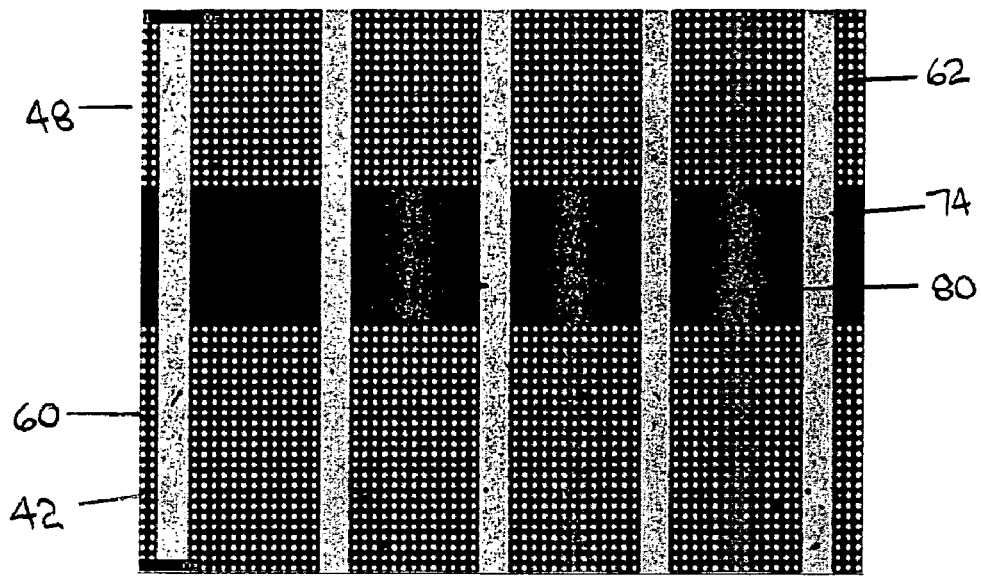
FIG. 42 is an exemplary transmittance image as would be collected for use in the Derivative Image Frequency Domain Method of the invention using a long embodiment of a fluid path.
Figure 43:
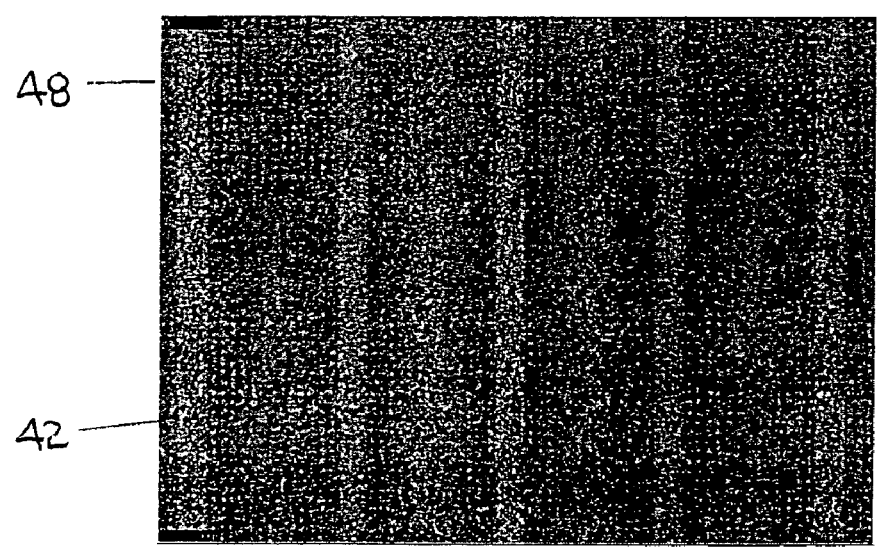
FIG. 43 is an exemplary derivative transmittance image as would be produced in the Derivative Image Frequency Domain Method.
Figure 44:
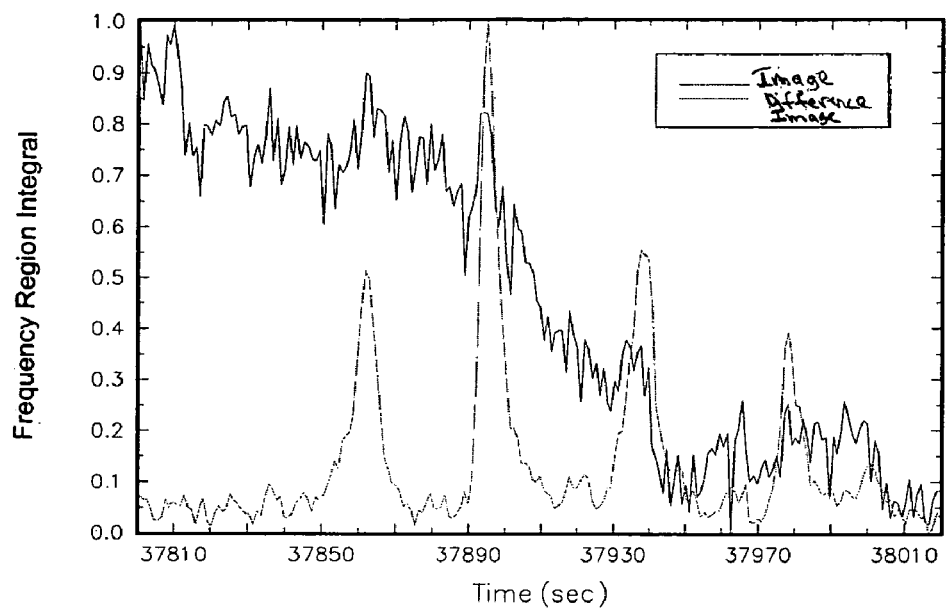
FIG. 44 is a graph depicting exemplary first relationships between frequency region integral and time as would be produced for both the Direct Frequency Domain Method and the Derivative Image Frequency Domain Method, in which the transmittance images are collected using a long embodiment of a fluid path.
Figure 45:
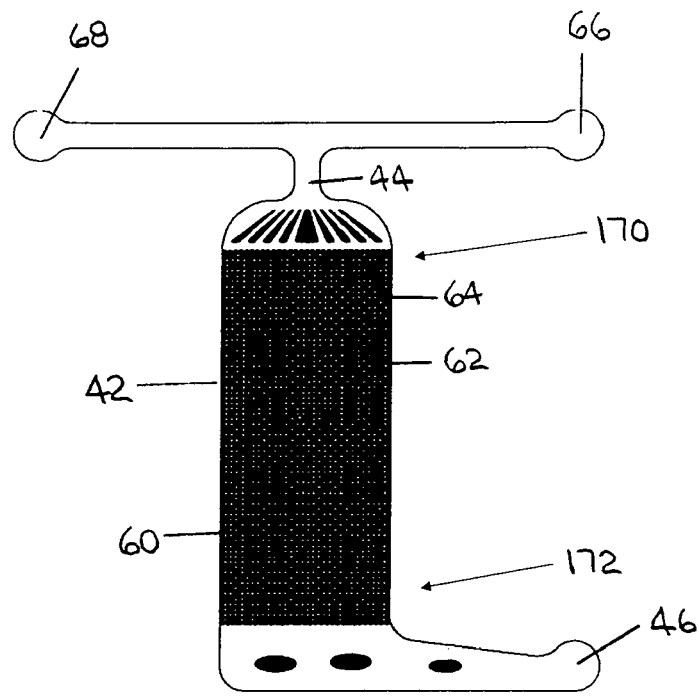
FIG. 45 is a schematic drawing of a short embodiment of a fluid path according to a preferred embodiment of the apparatus of the invention, indicating a first sampling section and a second sampling section.
Figure 46:
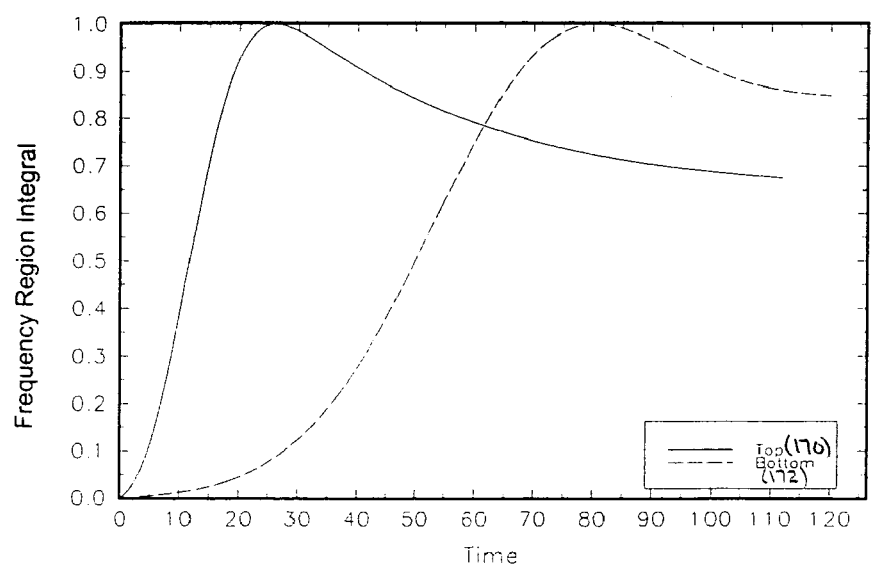
FIGS. 46-49 are exemplary graphs as would be produced in the Direct Frequency Domain Method of the invention, each depicting first relationships between frequency region integral and sampling time at the first sampling section and the second sampling section, for different values of pressure as the characterization variable.
Figure 47:
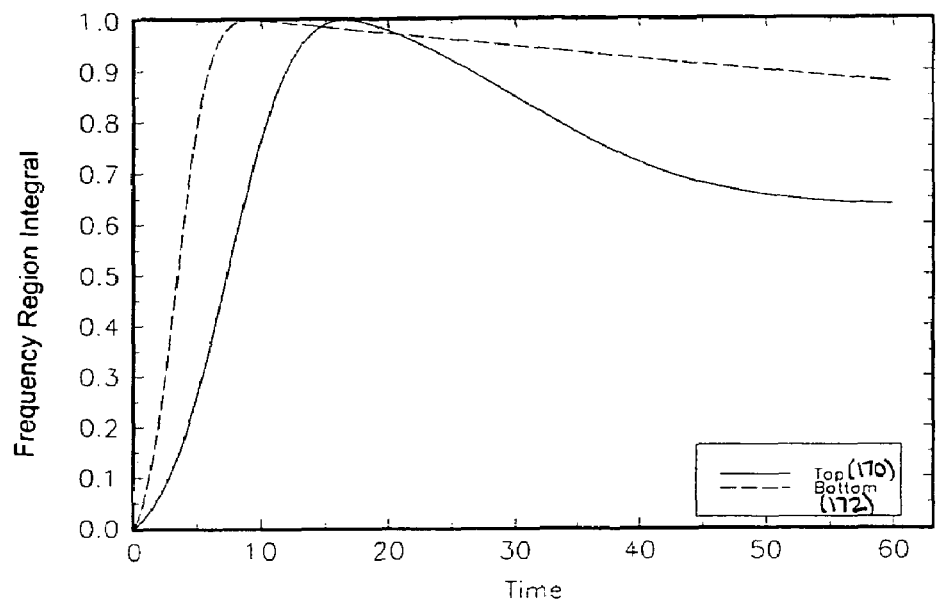
Figure 48:
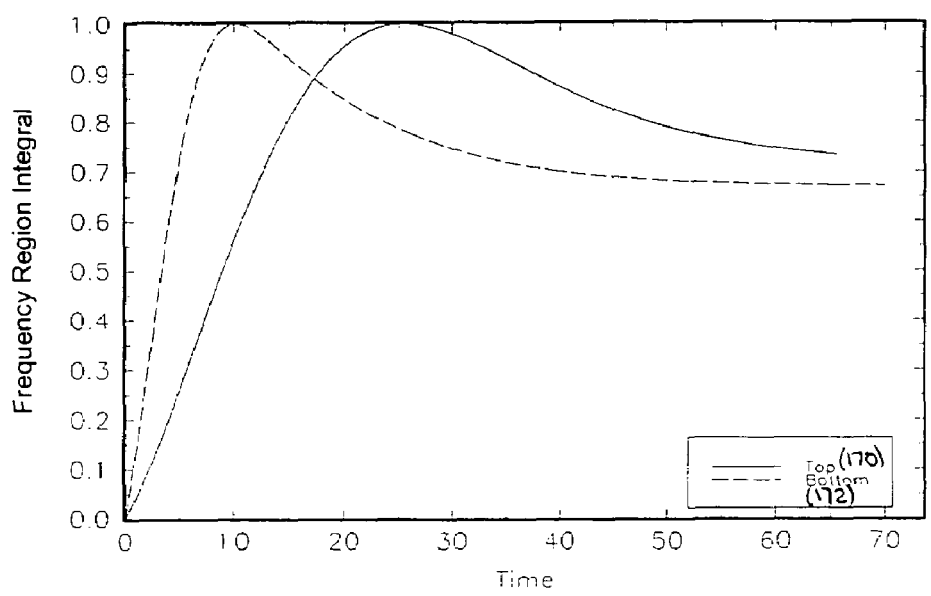
Figure 49:
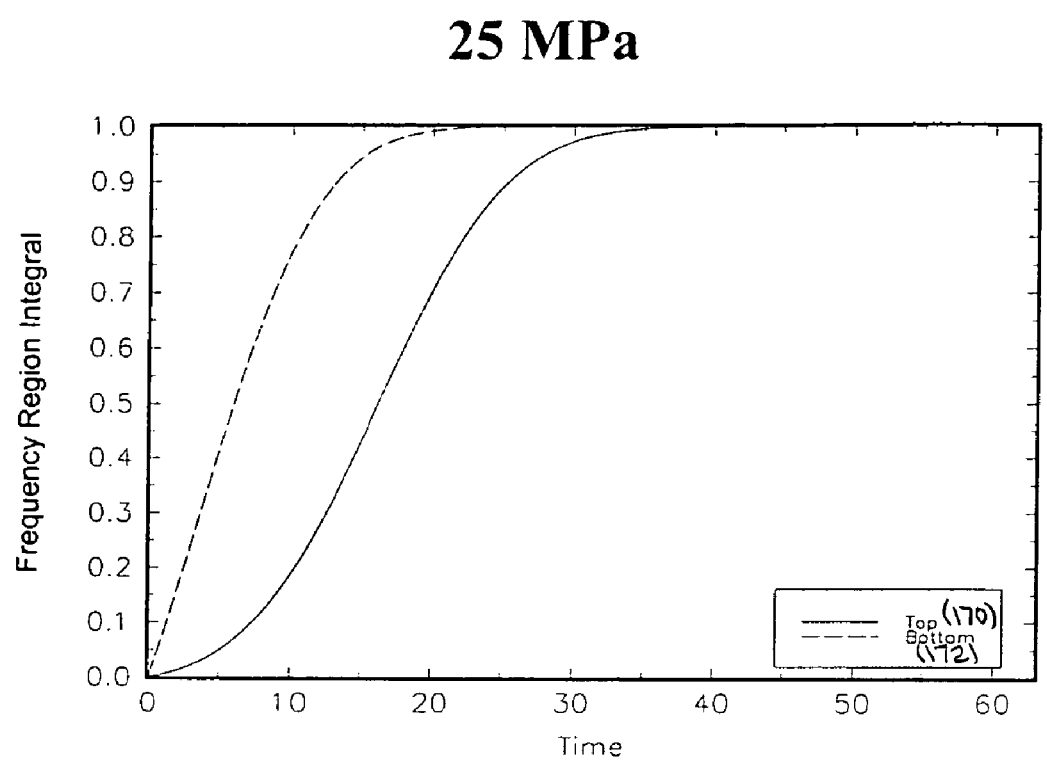

Referring to FIGS. 42-44, potential advantages of the Derivative Image Frequency Domain Method over the Direct Frequency Domain Method may be understood in the context of transmittance images collected using a long embodiment of a fluid path (42) of the type depicted in FIGS. 7-8.

Referring to FIG. 42, an exemplary transmittance image as would be collected using a long embodiment of a fluid path (42) is provided, and referring to FIG. 43, an exemplary corresponding derivative transmittance image as would be produced in the Derivative Image Frequency Domain Method is provided.

Referring to FIG. 44, two curves are depicted. One of the curves represents a plot of raw data points from a first relationship for the Direct Frequency Domain Method and the other of the curves represents a plot of raw data points from a first relationship for the Derivative Image Frequency Domain Method. The raw data points for both plots were obtained using the same set of transmittance images which were collected using a long embodiment of a fluid path (42).

As can be seen from FIG. 44, the plot for the Derivative Image Frequency Domain Method includes five very distinct peaks, while the peaks in the plot for the Direct Frequency Domain Method are somewhat obscured by "noise".

Referring to FIG. 42, it is noted that the sampling section (48) used in collecting the transmittance images spans five discrete longitudinal segments of the fluid path (42) in a long embodiment of the fluid path (42). As a result, the five peaks included in the plot for the Derivative Image Frequency Domain Method represent these five discrete longitudinal segments of the fluid path (42).

It is also noted that the five peaks included in the plot for the Derivative Image Frequency Domain Method have varying heights and areas. Since the discrete longitudinal segments of the fluid path (42) represent different time "phases" of the interaction between the hydrocarbon liquid and the solvent, the varying heights and areas of the peaks may possibly yield information regarding the nature of the interaction between the hydrocarbon liquid and the solvent. For example, the five peaks may assist in identifying single contact miscibility behaviour and multiple contact miscibility behaviour and may assist in determining specific characteristics of such miscibility behaviours.

Although the advantages of the Derivative Image Frequency Domain Method have been illustrated in FIGS. 42-44 with respect to transmittance images collected using a long embodiment of a fluid path (42), similar advantages may be expected where the transmittance images are collected using other embodiments of a fluid path (42).

Once the values of the general interfacial property factor are generated, the minimum miscibility pressure of the hydrocarbon liquid/solvent dispersion may be determined in order to characterize the interfacial property of the dispersion.

Regardless of how the values of the general interfacial property have been determined, characterizing the interfacial property of the dispersion (i.e., determining the minimum miscibility pressure of the dispersion) is achieved by determining a second relationship between the values of the general interfacial property factor and the pressures within the fluid path (42) at which the sets of transmittance images were collected and then using the second relationship to identify the minimum miscibility pressure.

Figure 28:
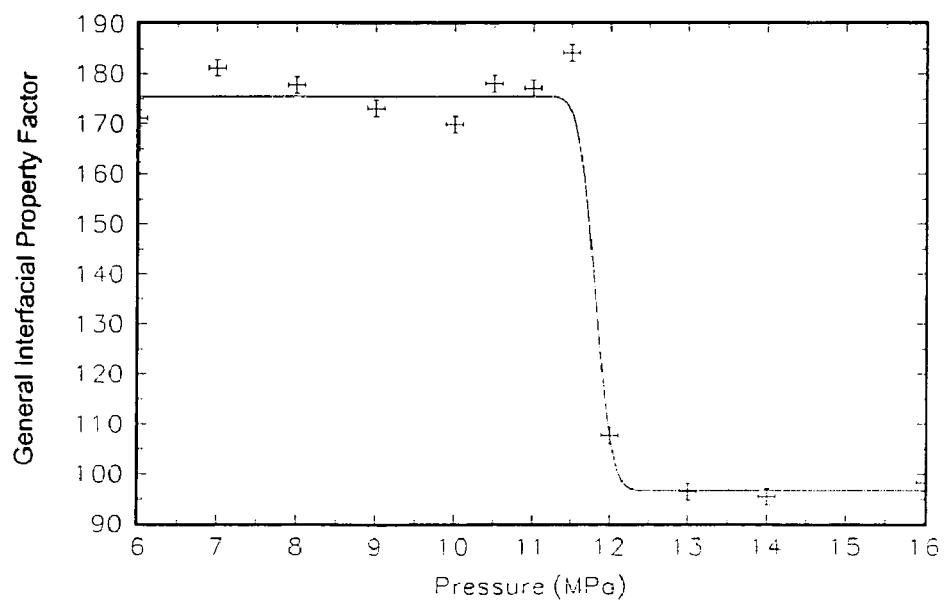
FIG. 28 is an exemplary graph as would be produced in the Direct Frequency Domain Method of the invention using a short embodiment of a fluid path, depicting a second relationship between general interfacial property factor and pressure.
Figure 41:
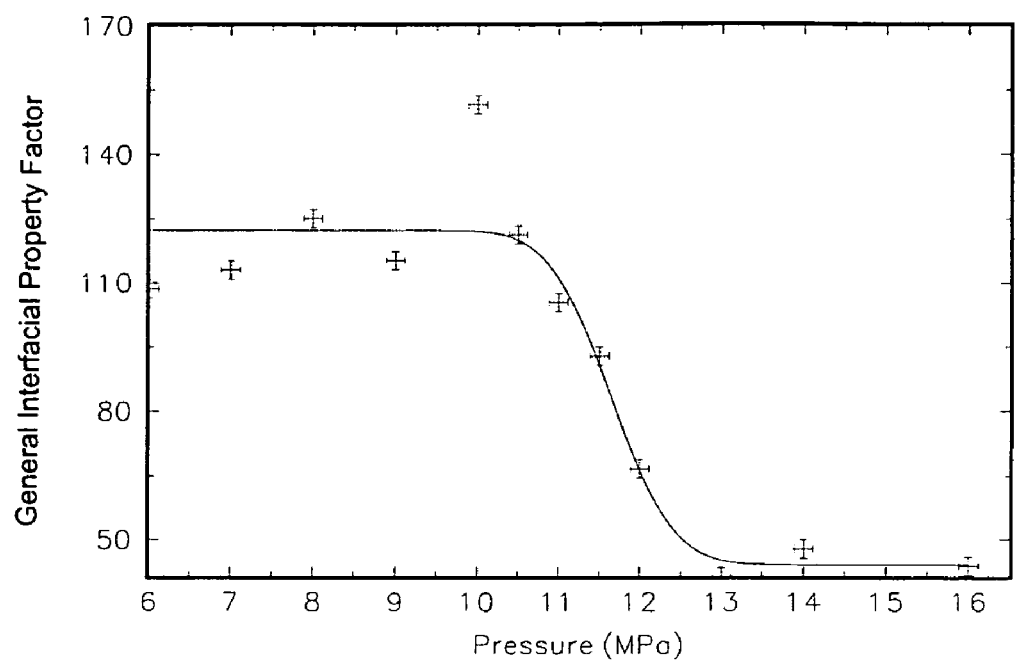
FIG. 41 is an exemplary graph as would be produced in the Direct Frequency Domain Method of the invention using a short embodiment of a fluid path, depicting a second relationship between general interfacial property factor and pressure.

Referring to each of FIGS. 14, 28 and 41, there are depicted curves which have been fit to data points representing values of the general interfacial property factor as a function of pressure of the dispersion. FIG. 14 depicts a curve in which the values of the general interfacial property factor have been generated using the Image Histogram Method. FIG. 28 depicts a curve in which the values of the general interfacial property factor have been generated using the Direct Frequency Domain Method. FIG. 41 depicts a curve in which the values of the general interfacial property factor have been generated using the Derivative Image Frequency Domain Method.

These curves represents the second relationship between the values of the general interfacial property factor and the pressures within the fluid path (42) at which the sets of transmittance images were collected. The curves may be fit to the data points using any suitable curve fitting technique. In the preferred embodiments the curves are fit to the data points using a non-linear least squares model according to the same general equation which is used in connection with the first relationship.

In FIGS. 14, 28 and 41, each of the curves exhibits an upper plateau and a lower plateau which are joined by a transition portion of the curve. Within the upper plateau the pressure of the dispersion is below the minimum miscibility pressure, with the result that the values of the general interfacial property factor are relatively high. Within the lower plateau the pressure of the dispersion is above the minimum miscibility pressure, with the result that the values of the general interfacial property factor are relatively low. Within the transition portion of the curve the values of the general interfacial property factor change rapidly and dramatically.

As a result, determining the minimum miscibility pressure of the dispersion is achieved by identifying from the second relationship a transition pressure, which transition pressure is used as the value of the minimum miscibility pressure of the dispersion.

The transition pressure may be identified from the second relationship using several methods or techniques. As a first example, the transition pressure may be identified as the pressure at which an asymptote of the transition portion of the curve representing the second relationship intersects the pressure axis of the curve. As a second example, the transition pressure may be identified as the pressure at which the slope of the curve representing the second relationship reaches a threshold value. As a third example, the transition pressure may be identified as the pressure at the beginning of the transition portion of the curve, the pressure at the end of the transition portion of the curve, or some pressure which is between the beginning and the end of the transition portion of the curve.

The method of the invention therefore uses image processing techniques in order to characterize an interfacial property of a dispersion.

In the preferred embodiments, the interfacial property to be characterized is the minimum miscibility pressure. The preferred embodiments could easily be adapted to characterize the minimum miscibility temperature by using temperature instead of pressure as the characterization variable. In addition to the preferred embodiments, the method of the invention may be used to characterize other interfacial properties of dispersions.

Additional functionality of the method may be achieved through the design of the fluid path (42) and the sampling section (48).

As one example, at least a portion of the fluid path (42) preferably includes the obstructions (62) which disrupt the flow of fluid through the fluid path (42) and thus enhance mixing of the constituent fluids of the dispersion. It has been discovered during testing of the method, however, that in some applications of the method at least a portion of the fluid path (42) within the sampling section (48) preferably does not include the obstructions (62), as exemplified by the embodiment of the fluid path (42) depicted in FIG. 7.

As a second example, the movement of the fluids through the fluid path (42) suggests several alternatives for configuring the sampling section (48).

In a first alternative for configuring the sampling section (48), the sampling section (48) may comprise a plurality of fixed discrete longitudinal segments of the fluid path (42) which are all included in the transmittance images so that the transmittance images can capture the effects which occur as the fluids pass through the fluid path (42), as exemplified by the embodiment of the fluid path (42) depicted in FIG. 7. As discussed above in connection with the Figures relating to the Derivative Image Frequency Domain Method, such effects may include single contact behaviour and multiple contact behaviour of the dispersion.

In a second alternative for configuring the sampling section (48), the sampling section (48) may be comprised of a single fixed longitudinal segment of the fluid path (42) so that the transmittance images capture only the effects which occur as the fluids pass through the single longitudinal segment, as exemplified by the embodiment of the fluid path (42) depicted in FIG. 9. This alternative provides the most simple information pertaining to the behaviour of the fluids in the fluid path (42).

In a third alternative for configuring the sampling section (48), the sampling section (48) may be movable so that the sampling section (48) moves with the fluids as they pass through the fluid path (42). This alternative facilitates observation of essentially the same fluid molecules over time as the constituents of the dispersion interact.

In a fourth alternative for configuring the sampling section (48), more than one sampling section (48) may be used in the method. For example, referring to FIGS. 45-49, a fluid path model (40) with a short embodiment of the fluid path (42) may include a first sampling section (170) adjacent to the inlet end (44) of the fluid path (42) and a second sampling section (172) adjacent to the outlet end (46) of the fluid path (42). Transmittance images may be collected from the sampling sections (170,172) simultaneously and independently. The first relationship and/or the second relationship identified from the first sampling section (170) may then be compared with the first relationship and/or the second relationship identified from the second sampling section (172), which comparison may provide information about the interaction of the fluids in the dispersion, including information about single contact behaviour and multiple contact behaviour.

Referring to FIGS. 46-49, curves representing the first relationship for the first sampling section (170) and the second sampling section (172) in a fluid path model (40) with a short embodiment of the fluid path (42) are depicted.

It is noted that the curves representing the first relationship for the first sampling section (170) have a more steep slope than the curves representing the first relationship for the second sampling section (172). The slopes of these curves may provide information about single contact behaviour and/or multiple contact behaviour of the dispersion.

The processing of the transmittance images in the method of the invention may be performed using many different apparatus and techniques. Preferably the processing of the images is performed at least in part using a suitably programmed computer, and is preferably performed using floating point arithmetic.

The embodiments of the invention in which an exclusive property or privilege is claimed are defined as follows:

1. A method for characterizing an interfacial property of a dispersion comprising a first fluid and a second fluid, the method comprising:
   (a) directing an electromagnetic radiation at the dispersion;
   (b) collecting over a sampling time period a set of transmittance images representing a spatial distribution of transmittance intensity of the electromagnetic radiation through the dispersion at a plurality of sampling times within the sampling time period, while maintaining a substantially constant value of a characterization variable relating to the dispersion;
   (c) repeating (a) and (b) one or more times at different values of the characterization variable in order to collect a plurality of sets of transmittance images, wherein each set of transmittance images is collected at a different value of the characterization variable;
   (d) generating from each of the sets of transmittance images a value of a general interfacial property factor for the dispersion, wherein each of the values of the general interfacial property factor is associated with different values of the characterization variable; and
   (e) characterizing the interfacial property of the dispersion using the values of the general interfacial property factor.

2. A method for characterizing an interfacial property of a dispersion comprising a first fluid and a second fluid, the method comprising:
   (a) providing a fluid path and a sampling section, the fluid path having an inlet end and an outlet end, the sampling section comprising at least a portion of the fluid path;
   (b) first introducing an initial amount of the first fluid into the fluid path so that the first fluid is contained within the fluid path;
   (c) second introducing an amount of the second fluid into the inlet end of the fluid path while maintaining a substantially constant value of a characterization variable within the fluid path in order to displace the first fluid from the fluid path at the outlet end of the fluid path;
   (d) directing an electromagnetic radiation at the sampling section;
   (e) collecting, over a sampling time period as the first fluid is displaced from the fluid path, a set of transmittance images representing a spatial distribution of transmittance intensity of the electromagnetic radiation through the sampling section at a plurality of sampling times within the sampling time period;
   (f) repeating (b) through (e) one or more times at different values of the characterization variable in order to collect a plurality of sets of transmittance images, wherein each set of transmittance images is collected at a different value of the characterization variable;
   (g) generating from each of the sets of transmittance images a value of a general interfacial property factor for the dispersion, wherein each of the values of the general interfacial property factor is associated with different values of the characterization variable; and
   (h) characterizing the interfacial property of the dispersion using the values of the general interfacial property factor.

3. The method as claimed in claim 2 wherein at least a portion of the fluid path is comprised of a porous fluid path.

4. The method as claimed in claim 3 wherein the porous fluid path is defined by an arrangement of obstructions in the fluid path.

5. The method as claimed in claim 4 wherein generating the value of the general interfacial property factor from each of the sets of transmittance images is comprised of producing a histogram representing each transmittance image and wherein each of the histograms provides a frequency relationship between transmittance intensity and frequency of transmittance intensity throughout the transmittance image at one of the sampling times.

6. The method as claimed in claim 5 wherein generating the value of the general interfacial property factor from each of the sets of transmittance images is further comprised of determining the value of the general interfacial property factor from the histograms.

7. The method as claimed in claim 6 wherein determining the value of the general interfacial property factor from the histograms is comprised of identifying in each of the histograms a peak representing transmittance intensity of the electromagnetic radiation through one of the first fluid and the second fluid and using the peaks to determine the value of the general interfacial property factor.

8. The method as claimed in claim 7 wherein determining the value of the general interfacial property factor from the histograms is further comprised of calculating a peak area for each of the peaks, determining a first relationship between the peak areas and the sampling times, and using the first relationship to determine the value of the general interfacial property factor.

9. The method as claimed in claim 8 wherein the value of the general interfacial property factor is an endpoint peak area which is identified from the first relationship.

10. The method as claimed in claim 8 wherein characterizing the interfacial property of the dispersion is comprised of determining a second relationship between the values of the general interfacial property factor and the values of the characterization variable and using the second relationship to characterize the interfacial property of the dispersion.

11. The method as claimed in claim 10 wherein the characterization variable is pressure, wherein the interfacial property of the dispersion to be characterized is a minimum miscibility pressure, wherein using the second relationship to characterize the interfacial property of the dispersion is comprised of identifying from the second relationship a transition pressure, and wherein the minimum miscibility pressure is the transition pressure.

12. The method as claimed in claim 11 wherein the first fluid is comprised of a liquid.

13. The method as claimed in claim 12 wherein the first fluid is comprised of a crude oil.

14. The method as claimed in claim 12 wherein the second fluid is comprised of a gas, a supercritical fluid, or mixtures thereof.

15. The method as claimed in claim 6 wherein determining the value of the general interfacial property factor from the histograms is comprised of identifying in each of the histograms a first peak representing transmittance intensity of the electromagnetic radiation through the first fluid and a second peak representing transmittance intensity of the electromagnetic radiation through the second fluid and using both the first peaks and the second peaks to determine the value of the general interfacial property factor.

16. The method as claimed in claim 15 wherein determining the value of the general interfacial property factor from the histograms is further comprised of calculating a first peak area for each of the first peaks, calculating a second peak area for each of the second peaks, determining a first relationship between the first peak areas, the second peak areas and the sampling times, and using the first relationship to determine the value of the general interfacial property factor.

17. The method as claimed in claim 16 wherein the value of the general interfacial property factor is an endpoint first peak area ratio which is identified from the first relationship.

18. The method as claimed in claim 17 wherein characterizing the interfacial property of the dispersion is comprised of determining a second relationship between the values of the general interfacial property factor and the values of the characterization variable and using the second relationship to characterize the interfacial property of the dispersion.

19. The method as claimed in claim 18 wherein the characterization variable is pressure, wherein the interfacial property of the dispersion to be characterized is a minimum miscibility pressure, wherein using the second relationship to characterize the interfacial property of the dispersion is comprised of identifying from the second relationship a transition pressure, and wherein the minimum miscibility pressure is the transition pressure.

20. The method as claimed in claim 19 wherein the first fluid is comprised of a liquid.

21. The method as claimed in claim 20 wherein the first fluid is comprised of a crude oil.

22. The method as claimed in claim 20 wherein the second fluid is comprised of a gas, a supercritical fluid, or mixtures thereof.

23. The method as claimed in claim 4 wherein generating the value of the general interfacial property factor from each of the sets of transmittance images is comprised of transforming each transmittance image into a frequency domain to produce a transformed transmittance image and wherein each of the transformed transmittance images provides a frequency relationship between transmittance intensity and frequency of transmittance intensity throughout the transmittance image at one of the sampling times.

24. The method as claimed in claim 23 wherein generating the value of the general interfacial property factor from each of the sets of transmittance images is further comprised of determining the value of the general interfacial property factor from the transformed transmittance images.

25. The method as claimed in claim 24 wherein determining the value of the general interfacial property factor from the transformed transmittance images is comprised of identifying in each of the transformed transmittance images a frequency region of interest and using the frequency regions of interest to determine the value of the general interfacial property factor.

26. The method as claimed in claim 25 wherein determining the value of the general interfacial property factor from the transformed transmittance images is further comprised of calculating a frequency region integral for the frequency region of interest of each of the transformed transmittance images, determining a first relationship between the frequency region integrals and the sampling times, and using the first relationship to determine the value of the general interfacial property factor.

27. The method as claimed in claim 26 wherein the value of the general interfacial property factor is an endpoint frequency region integral which is identified from the first relationship.

28. The method as claimed in claim 26 wherein characterizing the interfacial property of the dispersion is comprised of determining a second relationship between the values of the general interfacial property factor and the values of the characterization variable and using the second relationship to characterize the interfacial property of the dispersion.

29. The method as claimed in claim 28 wherein the characterization variable is pressure, wherein the interfacial property of the dispersion to be characterized is a minimum miscibility pressure, wherein using the second relationship to characterize the interfacial property of the dispersion is comprised of identifying from the second relationship a transition pressure, and wherein the minimum miscibility pressure is the transition pressure.

30. The method as claimed in claim 29 wherein the first fluid is comprised of a liquid.

31. The method as claimed in claim 30 wherein the first fluid is comprised of a crude oil.

32. The method as claimed in claim 30 wherein the second fluid is comprised of a gas, a supercritical fluid, or mixtures thereof.

33. The method as claimed in claim 25 wherein the frequency region of interest consists essentially of relatively low frequencies.

34. The method as claimed in claim 25 wherein the frequency region of interest is between zero and an upper frequency limit, so that frequencies above the upper frequency limit are excluded from the frequency region of interest.

35. The method as claimed in claim 34 wherein the transformed transmittance image has an area, wherein the frequency region of interest has an area, and wherein the upper frequency limit is selected so that a ratio of the area of the frequency region of interest to the area of the transformed transmittance image is no greater than about 0.25:1.

36. The method as claimed in claim 35 wherein the upper frequency limit is selected so that a ratio of the area of the frequency region of interest to the area of the transformed transmittance image is no greater than about 0.1:1.

37. The method as claimed in claim 4 wherein generating the value of the general interfacial property factor from each of the sets of transmittance images is comprised of producing a set of derivative transmittance images and wherein each of the derivative transmittance images represents a spatial distribution of a difference in transmittance intensity of the electromagnetic radiation between a pair of the transmittance images collected at a pair of the sampling times.

38. The method as claimed in claim 37 wherein generating the value of the general interfacial property factor from each of the sets of transmittance images is further comprised of transforming each derivative transmittance image into a frequency domain to produce a transformed derivative transmittance image and wherein each of the transformed derivative transmittance images provides a frequency relationship between the difference in transmittance intensity and frequency of the difference in transmittance intensity throughout the derivative transmittance image during a time interval defined by the pair of the sampling times.

39. The method as claimed in claim 38 wherein generating the value of the general interfacial property factor from each of the sets of transmittance images is further comprised of determining the value of the general interfacial property factor from the transformed derivative transmittance images.

40. The method as claimed in claim 39 wherein determining the value of the general interfacial property factor from the transformed derivative transmittance images is comprised of identifying in each of the transformed derivative transmittance images a frequency region of interest and using the frequency regions of interest to determine the value of the general interfacial property factor.

41. The method as claimed in claim 40 wherein determining the value of the general interfacial property factor from the transformed derivative transmittance images is further comprised of calculating a frequency region integral for the frequency region of interest of each of the transformed derivative transmittance images, determining a first relationship between the frequency region integrals and the sampling times and using the first relationship to determine the value of the general interfacial property factor.

42. The method as claimed in claim 41 wherein the value of the general interfacial property factor is an integral of the first relationship.

43. The method as claimed in claim 41 wherein characterizing the interfacial property of the dispersion is comprised of determining a second relationship between the values of the general interfacial property factor and the values of the characterization variable and using the second relationship to characterize the interfacial property of the dispersion.

44. The method as claimed in claim 43 wherein the characterization variable is pressure, wherein the interfacial property of the dispersion to be characterized is a minimum miscibility pressure, wherein using the second relationship to characterize the interfacial property of the dispersion is comprised of identifying from the second relationship a transition pressure, and wherein the minimum miscibility pressure is the transition pressure.

45. The method as claimed in claim 44 wherein the first fluid is comprised of a liquid.

46. The method as claimed in claim 45 wherein the first fluid is comprised of a crude oil.

47. The method as claimed in claim 45 wherein the second fluid is comprised of a gas, a supercritical fluid, or mixtures thereof.

48. The method as claimed in claim 40 wherein the frequency region of interest consists essentially of relatively low frequencies.

49. The method as claimed in claim 40 wherein the frequency region of interest is between zero and an upper frequency limit, so that frequencies above the upper frequency limit are excluded from the frequency region of interest.

50. The method as claimed in claim 49 wherein the transformed derivative transmittance image has an area, wherein the frequency region of interest has an area, and wherein the upper frequency limit is selected so that a ratio of the area of the frequency region of interest to the area of the transformed derivative transmittance image is no greater than about 0.25:1.

51. The method as claimed in claim 50 wherein the upper frequency limit is selected so that a ratio of the area of the frequency region of interest to the area of the transformed derivative transmittance image is no greater than about 0.1:1.

52. The method as claimed in claim 4, further comprising, before generating the values of the general interfacial property factor from the sets of transmittance images, processing the sets of transmittance images to provide an intensity spatial correction of the sets of transmittance images to account for variations in a spatial distribution of intensity of the electromagnetic radiation being directed at the sampling section of the fluid path.

53. The method as claimed in claim 52 wherein processing the sets of transmittance images to provide the intensity spatial correction is comprised of collecting a background transmittance image representing a spatial distribution of transmittance intensity of the electromagnetic radiation through the sampling section without influence from the first fluid and the second fluid and using the background transmittance image to normalize each of the transmittance images.

54. The method as claimed in claim 4, further comprising, before generating the values of the general interfacial property factor from the sets of transmittance images, processing the sets of transmittance images to provide an intensity time correction of the sets of transmittance images to account for variations over time in the intensity of the electromagnetic radiation being directed at the sampling section of the fluid path.

55. The method as claimed in claim 54 wherein processing the sets of transmittance images to provide the intensity time correction is comprised of producing a histogram representing each of the transmittance images, wherein each of the histograms provides a relationship between transmittance intensity and frequency of transmittance intensity throughout the transmittance image at one of the sampling times.

56. The method as claimed in claim 55 wherein processing the sets of transmittance images to provide the intensity time correction is further comprised of processing each of the histograms to produce cumulative frequency distributions for each of the histograms, wherein each of the cumulative frequency distributions provides a relationship between transmittance intensity and frequency of transmittance intensity throughout the transmittance image at one of the sampling times, processing each of the cumulative frequency distributions below a lower cumulative frequency threshold, and processing each of the cumulative frequency distributions above an upper cumulative frequency threshold.

57. The method as claimed in claim 56 wherein processing the sets of transmittance images to provide the intensity time correction is further comprised of determining a lower limit transmittance intensity for each of the cumulative frequency distributions at the lower cumulative frequency threshold, adjusting transmittance intensities below the lower limit transmittance intensity in each of the cumulative frequency distributions to the lower limit transmittance intensity, determining an upper limit transmittance intensity for each of the cumulative frequency distributions at the upper cumulative frequency threshold, adjusting transmittance intensities above the upper limit transmittance intensity in each of the cumulative frequency distributions to the upper limit transmittance intensity, and regenerating the sets of transmittance images using the adjusted transmittance intensities so that the regenerated sets of transmittance images include the intensity time correction.

* * * * *